United States Patent [19]

Thomas et al.

[11] Patent Number: 5,436,392

[45] Date of Patent: Jul. 25, 1995

[54] **TRANSGENIC PLANTS EXPRESSING *M. SEXTA* PROTEASE INHIBITOR**

[75] Inventors: John C. Thomas; Hans J. Bohnert, both of Tucson, Ariz.; Michael R. Kanost, Manhattan, Kans.

[73] Assignee: Arizona Technology Development Corporation, Tucson, Ariz.

[21] Appl. No.: 994,133

[22] Filed: Dec. 21, 1992

Related U.S. Application Data

[63] Continuation-in-part of Ser. No. 464,310, Jan. 12, 1990, Pat. No. 5,196,304.

[51] Int. Cl.$^6$ ............... A01H 5/00; A01N 25/00; C12N 15/00; C07H 17/00
[52] U.S. Cl. ............... 800/205; 800/200; 800/255; 800/DIG. 24; 800/DIG. 27; 800/DIG. 43; 424/405; 935/11; 536/23.1; 536/23.5; 435/69.1; 435/70.1; 435/172.3
[58] Field of Search ............ 435/170.1, 172.3, 69.1, 435/70.1; 424/405; 800/200, 205, 255, DIG. 27, DIG. 40, DIG. 43, DIG. 44, DIG. 24; 935/11, 22; 47/58.06; 536/23.1, 23.5

[56] References Cited

U.S. PATENT DOCUMENTS 5,196,304  3/1993  Kanost et al. ............ 435/6

FOREIGN PATENT DOCUMENTS 0135343  8/1984  European Pat. Off. .

OTHER PUBLICATIONS

Saul et al. 1986 FEBS 4054. 208(1):113–116.
Sanchez-Serrano et al. 1987. The EMBO Journal 6(2): 303–306.
Ramesh et al. 1988. The Journal of Biological Chemistry. 263(23): 11523–11527.
Potrykus. 1991. Annu. Rev. Plant Physiol. Plant Mol. Biology. 42:205–225.
Jaye et al. 1983. Nucleic Acids Research. 11(8):2325–2335.
Matsuda et al. 1981. FEBS Letters. 126(1):111–113.
Broadway, R. M. and Duffey, S. S. (1986) *J. Insect Physiol.* 32(10):827–833.
Gatehouse, A. M. R. et al. (1980) *Phytochemistry* 19:751–756.
Hilder, V. A. et al. (1987) *Nature* 330:160–163.
Johnson, R. et al. (1989) *Proc. Natl. Acad. Sci. USA* 86:9871–9875.
Pusztai, A. et al. (1992) *Brit. J. Nutrition* 68:783–791.
Steffens, R. et al. (1978) *J. Agric. Food Chem.* 26:170–174.
Thomas, J. C. et al. (1990) *Abstracts VIIth International Congress on Plant Tissue and Cell Culture*, held Jun. 24–29, 1990, Amsterdam, Abstract A2-137, p. 78.
Thomas, J. C. et al. (1992) Plant Physiology 99:47.
*First Annual Review of the 5-year National Research and Action Plan for Development of Management and Control of the Sweetpotato Whitefly*, held Jan. 18,21, 1993, Tempe, Ariz., 147 pp.
Boswell, D. R. et al. (1988) "Genetic Engineering and the Serpins," BioEssays 8:83–87.

*Primary Examiner*—David T. Fox
*Assistant Examiner*—Erich E. Veitenheimer
*Attorney, Agent, or Firm*—Greenlee and Winner

[57] ABSTRACT

This invention relates to a protease inhibitor of the insect *Manduca sexta*, its purification, cloning of a DNA sequence encoding the inhibitor, modifications to change inhibitor specificity, transgenic plants carrying and expressing said DNA sequence and insect resistance conferred thereby on said transgenic plants.

16 Claims, 7 Drawing Sheets

```
   1 GAGTGGGACGTTCGGCACAGCAACATGAAGATTATTATGTGTATATTTGGCCTTGCGGCC
 -16                           M  K  I  I  M  C  I  F  G  L  A  A

61 TTGGCCATGGCTGGCGAGACGGATCTGCAGAAGATTTTACGAGAAAGCAACGACCAATTT
  -4  L  A  M  A  G  E  T  D  L  Q  K  I  L  R  E  S  N  D  Q  F
              -1 +1

121 ACAGCCCAGATGTTTTCTGAAGTGGTAAAAGCGAACCCTGGTCAAACGTCGTGTTGTCT
  17  T  A  Q  M  F  S  E  V  V  K  A  N  P  G  Q  N  V  V  L  S

181 GCATTCTCCGTCCTGCCACCATTGGGCCAACTGGCTTTGGCTTCCGTAGGTGAATCACAC
  37  A  F  S  V  L  P  P  L  G  Q  L  A  L  A  S  V  G  E  S  H

241 GACGAACTGCTAAGAGCTTTGGCTTTACCCAACGACAATGTGACGAAAGATGTATTTGCG
  57  D  E  L  L  R  A  L  A  L  P  N  D  N  V  T  K  D  V  F  A

301 GATCTAAACCGTGGTGTGCGAGCTGTCAAAGGAGTCGATCTGAAGATGGCCAGTAAAATT
  77  D  L  N  R  G  V  R  A  V  K  G  V  D  L  K  M  A  S  K  I

361 TATGTAGCAAAAGGTCTTGAACTTAATGATGACTTCGCGGCAGTATCAAGAGACGTTTTC
  97  Y  V  A  K  G  L  E  L  N  D  D  F  A  A  V  S  R  D  V  F

421 GGTTCTGAAGTCCAAAATGTAGACTTTGTAAAGAGCGTTGAAGCAGCCGGCGCGATTAAC
 117  G  S  E  V  Q  N  V  D  F  V  K  S  V  E  A  A  G  A  I  N

481 AAATGGGTTGAAGATCAAACCAACAATCGCATCAAAAATTTAGTCGACCCAGATGCGTTG
 137  K  W  V  E  D  Q  T  N  N  R  I  K  N  L  V  D  P  D  A  L

541 GACGAAACAACACGCTCCGTTCTCGTCAATGCTATATACTTCAAGGGTAGCTGGAAAGAC
 157  D  E  T  T  R  S  V  L  V  N  A  I  Y  F  K  G  S  W  K  D

601 AAGTTTGTCAAGGAAAGAACAATGGACAGAGACTTCCATGTTTCCAAAGACAAAACAATT
 177  K  F  V  K  E  R  T  M  D  R  D  F  H  V  S  K  D  K  T  I

661 AAAGTGCCTACTATGATCGGTAAGAAGGATGTCCGTTACGCTGATGTTCCTGAACTTGAT
 197  K  V  P  T  M  I  G  K  K  D  V  R  Y  A  D  V  P  E  L  D

721 GCTAAGATGATTGAAATGTCATATGAGGGTGACCAAGCATCTATGATTATTATATTACCC
 217  A  K  M  I  E  M  S  Y  E  G  D  Q  A  S  M  I  I  I  L  P

781 AACCAAGTAGACGGAATCACAGCACTGGAACAAAAACTGAAGGATCCTAAAGCTCTTTCA
 237  N  Q  V  D  G  I  T  A  L  E  Q  K  L  K  D  P  K  A  L  S

841 AGAGCTGAGGAGCGTTTGTACAACACTGAAGTTGAAATTTACCTTCCAAAATTCAAAATT
 257  R  A  E  E  R  L  Y  N  T  E  V  E  I  T  L  P  K  F  K  I

901 GAAACAACTACCGATCTGAAAGAAGTTCTTAGTAACATGAACATCAAAAAATTGTTCACT
 277  E  T  T  T  D  L  K  E  V  L  S  N  M  N  I  K  K  L  F  T

961 CCAGGAGCAGCTAGACTAGAGAATCTTTTAAAAACAAAGGAATCTTTATATGTAGATGCG
 297  P  G  A  A  R  L  E  N  L  L  K  T  K  E  S  L  T  V  D  A

1021 GCTATACAAAAAGCTTTTATCGAAGTCAACGAAGAAGGTGCAGAGGCTGCGGCTGCTAAC
 317  A  I  Q  K  A  F  I  E  V  N  E  E  G  A  E  A  A  A  N

1081 GCTTTCGGTATCGTACCGGCGAGTTTGATACTATATCCAGAAGTTCATATCGATCGACCT
 337  A  F  G  I  V  P  A  S  L  I  L  T  P  E  V  H  I  D  R  P

1141 TTCTACTTTGAACTTAAGATTGATGGTATCCCCATGTTCAACGGCAAAGTTATCGAACCT
 357  F  Y  F  E  L  K  I  D  G  I  P  M  F  N  G  K  V  I  E  P

1201 TAATGCTTTCTTTATTATAGAATCATATTCTTCGTATGAACCTGTCGTACCCGTCTTTGA
     ---

1261 CATAGATAAACCTTTTTACTTCAACATAAGAGCTAATGGCCAGTCTTTGTTCAACGGGCT

1321 ATGTTTCCAACCATAAAACGATATATTGTTATCATTAAGAAACATTAACAATAACGTCCG

1381 GTTGGAATGTAATCAAATCACTTTTATACAAACAATAAACATTTTCT
```

FIG. 3

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1427 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..1203

( i x ) FEATURE:
        ( A ) NAME/KEY: matpeptide
        ( B ) LOCATION: 73..1200

( i x ) FEATURE:
        ( A ) NAME/KEY: sigpeptide
        ( B ) LOCATION: 25..72

( x i ) SEQUENCE DESCRIPTION: SEQ ID NO:1:

```
GAGTGGGACG TTCGGCACAG CAAC ATG AAG ATT ATT ATG TGT ATA TTT GGC            51
                          Met Lys Ile Ile Met Cys Ile Phe Gly
                          -16 -15              -10

CTT GCG GCC TTG GCC ATG GCT GGC GAG ACG GAT CTG CAG AAG ATT TTA           99
Leu Ala Ala Leu Ala Met Ala Gly Glu Thr Asp Leu Gln Lys Ile Leu
        -5              1               5

CGA GAA AGC AAC GAC CAA TTT ACA GCC CAG ATG TTT TCT GAA GTG GTA          147
Arg Glu Ser Asn Asp Gln Phe Thr Ala Gln Met Phe Ser Glu Val Val
 10              15              20                          25

AAA GCG AAC CCT GGT CAA AAC GTC GTG TTG TCT GCA TTC TCC GTC CTG          195
Lys Ala Asn Pro Gly Gln Asn Val Val Leu Ser Ala Phe Ser Val Leu
                 30              35                          40

CCA CCA TTG GGC CAA CTG GCT TTG GCT TCC GTA GGT GAA TCA CAC GAC          243
Pro Pro Leu Gly Gln Leu Ala Leu Ala Ser Val Gly Glu Ser His Asp
             45              50                      55

GAA CTG CTA AGA GCT TTG GCT TTA CCC AAC GAC AAT GTG ACG AAA GAT          291
Glu Leu Leu Arg Ala Leu Ala Leu Pro Asn Asp Asn Val Thr Lys Asp
         60              65                  70

GTA TTT GCG GAT CTA AAC CGT GGT GTG CGA GCT GTC AAA GGA GTC GAT          339
Val Phe Ala Asp Leu Asn Arg Gly Val Arg Ala Val Lys Gly Val Asp
     75              80              85

CTG AAG ATG GCC AGT AAA ATT TAT GTA GCA AAA GGT CTT GAA CTT AAT          387
Leu Lys Met Ala Ser Lys Ile Tyr Val Ala Lys Gly Leu Glu Leu Asn
 90              95              100                         105

GAT GAC TTC GCG GCA GTA TCA AGA GAC GTT TTC GGT TCT GAA GTC CAA          435
Asp Asp Phe Ala Ala Val Ser Arg Asp Val Phe Gly Ser Glu Val Gln
             110             115                     120

AAT GTA GAC TTT GTA AAG AGC GTT GAA GCA GCC GGC GCG ATT AAC AAA          483
Asn Val Asp Phe Val Lys Ser Val Glu Ala Ala Gly Ala Ile Asn Lys
         125             130                 135

TGG GTT GAA GAT CAA ACC AAC AAT CGC ATC AAA AAT TTA GTC GAC CCA          531
Trp Val Glu Asp Gln Thr Asn Asn Arg Ile Lys Asn Leu Val Asp Pro
     140             145                 150

GAT GCG TTG GAC GAA ACA ACA CGC TCC GTT CTC GTC AAT GCT ATA TAC          579
Asp Ala Leu Asp Glu Thr Thr Arg Ser Val Leu Val Asn Ala Ile Tyr
 155             160                 165

TTC AAG GGT AGC TGG AAA GAC AAG TTT GTC AAG GAA AGA ACA ATG GAC          627
Phe Lys Gly Ser Trp Lys Asp Lys Phe Val Lys Glu Arg Thr Met Asp
170              175                 180                 185

AGA GAC TTC CAT GTT TCC AAA GAC AAA ACA ATT AAA GTG CCT ACT ATG          675
```

```
Arg Asp Phe His Val Ser Lys Asp Lys Thr Ile Lys Val Pro Thr Met
            190             195                 200

ATC GGT AAG AAG GAT GTC CGT TAC GCT GAT GTT CCT GAA CTT GAT GCT      723
Ile Gly Lys Lys Asp Val Arg Tyr Ala Asp Val Pro Glu Leu Asp Ala
            205             210             215

AAG ATG ATT GAA ATG TCA TAT GAG GGT GAC CAA GCA TCT ATG ATT ATT      771
Lys Met Ile Glu Met Ser Tyr Glu Gly Asp Gln Ala Ser Met Ile Ile
            220             225             230

ATA TTA CCC AAC CAA GTA GAC GGA ATC ACA GCA CTG GAA CAA AAA CTG      819
Ile Leu Pro Asn Gln Val Asp Gly Ile Thr Ala Leu Glu Gln Lys Leu
            235             240             245

AAG GAT CCT AAA GCT CTT TCA AGA GCT GAG GAG CGT TTG TAC AAC ACT      867
Lys Asp Pro Lys Ala Leu Ser Arg Ala Glu Glu Arg Leu Tyr Asn Thr
250             255             260             265

GAA GTT GAA ATT TAC CTT CCA AAA TTC AAA ATT GAA ACA ACT ACC GAT      915
Glu Val Glu Ile Tyr Leu Pro Lys Phe Lys Ile Glu Thr Thr Thr Asp
            270             275             280

CTG AAA GAA GTT CTT AGT AAC ATG AAC ATC AAA AAA TTG TTC ACT CCA      963
Leu Lys Glu Val Leu Ser Asn Met Asn Ile Lys Lys Leu Phe Thr Pro
            285             290             295

GGA GCA GCT AGA CTA GAG AAT CTT TTA AAA ACA AAG GAA TCT TTA TAT     1011
Gly Ala Ala Arg Leu Glu Asn Leu Leu Lys Thr Lys Glu Ser Leu Tyr
            300             305             310

GTA GAT GCG GCT ATA CAA AAA GCT TTT ATC GAA GTC AAC GAA GAA GGT     1059
Val Asp Ala Ala Ile Gln Lys Ala Phe Ile Glu Val Asn Glu Glu Gly
            315             320             325

GCA GAG GCT GCG GCT GCT AAC GCT TTC GGT ATC GTA CCG GCG AGT TTG     1107
Ala Glu Ala Ala Ala Ala Asn Ala Phe Gly Ile Val Pro Ala Ser Leu
330             335             340             345

ATA CTA TAT CCA GAA GTT CAT ATC GAT CGA CCT TTC TAC TTT GAA CTT     1155
Ile Leu Tyr Pro Glu Val His Ile Asp Arg Pro Phe Tyr Phe Glu Leu
            350             355             360

AAG ATT GAT GGT ATC CCC ATG TTC AAC GGC AAA GTT ATC GAA CCT TAATGCTT 1210
Lys Ile Asp Gly Ile Pro Met Phe Asn Gly Lys Val Ile Glu Pro
            365             370             375

TTTATTATAG AATCATATTC TTCGTATGAA CCTGTCGTAC CCGTCTTTGA CATAGATAAA    1270

CCTTTTTACT TCAACATAAG AGCTAATGGC CAGTCTTTGT TCAACGGGCT ATGTTTCCAA    1330

CCATAAAACG ATATATTGTT ATCATTAAGA AACATTAACA ATAACGTCCG GTTGGAATGT    1390

AATCAAATCA CTTTTATACA AACAATAAAC ATTTTCT                             1427
```

(2) INFORMATION FOR SEQ ID NO:2:

(i) SEQUENCE CHARACTERISTICS:
        (A) LENGTH: 392 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ile Ile Met Cys Ile Phe Gly Leu Ala Ala Leu Ala Met Ala
-16 -15             -10                  -5

Gly Glu Thr Asp Leu Gln Lys Ile Leu Arg Glu Ser Asn Asp Gln Phe
 1           5               10              15

Thr Ala Gln Met Phe Ser Glu Val Val Lys Ala Asn Pro Gly Gln Asn
            20              25              30

Val Val Leu Ser Ala Phe Ser Val Leu Pro Pro Leu Gly Gln Leu Ala
            35              40              45

Leu Ala Ser Val Gly Glu Ser His Asp Glu Leu Leu Arg Ala Leu Ala
        50              55              60
```

-continued

| | | | | | | | | | | | | | | | |
|---|---|---|---|---|---|---|---|---|---|---|---|---|---|---|---|
| Leu | Pro | Asn | Asp | Asn | Val | Thr | Lys | Asp | Val | Phe | Ala | Asp | Leu | Asn | Arg |
| 65 | | | | 70 | | | | 75 | | | | | | | 80 |
| Gly | Val | Arg | Ala | Val | Lys | Gly | Val | Asp | Leu | Lys | Met | Ala | Ser | Lys | Ile |
| | | | | 85 | | | | 90 | | | | | 95 | | |
| Tyr | Val | Ala | Lys | Gly | Leu | Glu | Leu | Asn | Asp | Asp | Phe | Ala | Ala | Val | Ser |
| | | | 100 | | | | | 105 | | | | | 110 | | |
| Arg | Asp | Val | Phe | Gly | Ser | Glu | Val | Gln | Asn | Val | Asp | Phe | Val | Lys | Ser |
| | | 115 | | | | | 120 | | | | | 125 | | | |
| Val | Glu | Ala | Ala | Gly | Ala | Ile | Asn | Lys | Trp | Val | Glu | Asp | Gln | Thr | Asn |
| | 130 | | | | | 135 | | | | | 140 | | | | |
| Asn | Arg | Ile | Lys | Asn | Leu | Val | Asp | Pro | Asp | Ala | Leu | Asp | Glu | Thr | Thr |
| 145 | | | | | 150 | | | | | 155 | | | | | 160 |
| Arg | Ser | Val | Leu | Val | Asn | Ala | Ile | Tyr | Phe | Lys | Gly | Ser | Trp | Lys | Asp |
| | | | | 165 | | | | | 170 | | | | | 175 | |
| Lys | Phe | Val | Lys | Glu | Arg | Thr | Met | Asp | Arg | Asp | Phe | His | Val | Ser | Lys |
| | | | 180 | | | | | 185 | | | | | 190 | | |
| Asp | Lys | Thr | Ile | Lys | Val | Pro | Thr | Met | Ile | Gly | Lys | Lys | Asp | Val | Arg |
| | | 195 | | | | | 200 | | | | | 205 | | | |
| Tyr | Ala | Asp | Val | Pro | Glu | Leu | Asp | Ala | Lys | Met | Ile | Glu | Met | Ser | Tyr |
| | 210 | | | | | 215 | | | | | 220 | | | | |
| Glu | Gly | Asp | Gln | Ala | Ser | Met | Ile | Ile | Ile | Leu | Pro | Asn | Gln | Val | Asp |
| 225 | | | | | 230 | | | | | 235 | | | | | 240 |
| Gly | Ile | Thr | Ala | Leu | Glu | Gln | Lys | Leu | Lys | Asp | Pro | Lys | Ala | Leu | Ser |
| | | | | 245 | | | | | 250 | | | | | 255 | |
| Arg | Ala | Glu | Glu | Arg | Leu | Tyr | Asn | Thr | Glu | Val | Glu | Ile | Tyr | Leu | Pro |
| | | | | 260 | | | | | 265 | | | | | 270 | |
| Lys | Phe | Lys | Ile | Glu | Thr | Thr | Thr | Asp | Leu | Lys | Glu | Val | Leu | Ser | Asn |
| | | | 275 | | | | | 280 | | | | | 285 | | |
| Met | Asn | Ile | Lys | Lys | Leu | Phe | Thr | Pro | Gly | Ala | Ala | Arg | Leu | Glu | Asn |
| | 290 | | | | | 295 | | | | | 300 | | | | |
| Leu | Leu | Lys | Thr | Lys | Glu | Ser | Leu | Tyr | Val | Asp | Ala | Ala | Ile | Gln | Lys |
| 305 | | | | | 310 | | | | | 315 | | | | | 320 |
| Ala | Phe | Ile | Glu | Val | Asn | Glu | Glu | Gly | Ala | Glu | Ala | Ala | Ala | Ala | Asn |
| | | | | 325 | | | | | 330 | | | | | 335 | |
| Ala | Phe | Gly | Ile | Val | Pro | Ala | Ser | Leu | Ile | Leu | Tyr | Pro | Glu | Val | His |
| | | | 340 | | | | | 345 | | | | | 350 | | |
| Ile | Asp | Arg | Pro | Phe | Tyr | Phe | Glu | Leu | Lys | Ile | Asp | Gly | Ile | Pro | Met |
| | | 355 | | | | | 360 | | | | | 365 | | | |
| Phe | Asn | Gly | Lys | Val | Ile | Glu | Pro | | | | | | | | |
| | 370 | | | | | 375 | | | | | | | | | |

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Pro  Met  Ser  Ile  Pro  Pro
    1                      5

( 2 ) INFORMATION FOR SEQ ID NO:4:

( i ) SEQUENCE CHARACTERISTICS:
        ( A ) LENGTH: 6 amino acids
        ( B ) TYPE: amino acid (C) STRANDEDNESS: single
        (D) TOPOLOGY: linear (ii) MOLECULE TYPE: protein (xi) SEQUENCE DESCRIPTION: SEQ ID NO:4:

Leu Leu Ser Ala Leu Val
   1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Gly Arg Ser Leu Asn Pro
   1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Arg Lys Ala Ile Leu Pro
   1               5

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Ala Ser Val Ser Glu
   1               5

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Pro Ala Ser Leu Ile Leu
   1               5

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: double
        (D) TOPOLOGY: linear ( i i ) MOLECULE TYPE: DNA (genomic)

( x i ) SEQUENCE DESCRIPTION: SEQ ID NO:9:

GGTATCGTAC CGGCGAGTTT GATACTA                27

(2) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

Gly Ile Val Pro Ala Ser Leu Ile Leu
1               5

(2) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

GGTATCGTAC CGTTTAGTTT GATACTA                27

(2) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Gly Ile Val Pro Phe Ser Leu Ile Leu
1               5

(2) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

GGTATCGTAC CGAAGAGTTT GATACTA                27

(2) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Gly Ile Val Pro Lys Ser Leu Ile Leu
1               5
```

(2) INFORMATION FOR SEQ ID NO:15:

(i) SEQUENCE CHARACTERISTICS:
(A) LENGTH: 11 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:15:

CTATGATCAT G                                                                 11

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

GGCGAGACGG ATCTGCAGAA                                                        20

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

CGCTCCTCAG CTCTTGAAAG                                                        20

TRANSGENIC PLANTS EXPRESSING *M. SEXTA* PROTEASE INHIBITOR

This is a continuation-in-part of application Ser. No. 07/464,310, filed Jan. 12, 1990, now U.S. Pat. No. 5,196,304.

BACKGROUND OF THE INVENTION

The present invention relates to a protease inhibitor of the insect *Manduca sexta*, its purification, cloning of a DNA sequence encoding the inhibitor, modifications to change inhibitor specificity, transgenic plants carrying and expressing said DNA sequence and insect resistance conferred thereby on said transgenic pants.

The serpins are a superfamily of serine proteinase inhibitors. Human plasma contains serpins which are similar in amino acid sequence and mechanism of inhibition, but differ in their specificity toward proteolytic enzymes. The serpin superfamily includes proteins of about $M_r=50,000–100,000$, which function in regulation of blood clotting (antithrombin-III, heparin cofactor-II, antiplasmin, protein C inhibitor), complement activation (C1 inhibitor), and proteinases released from neutrophils ($\alpha_1$-antitrypsin, $\alpha_1$-antichymotrypsin). The serpin superfamily also includes endothelial plasminogen activator inhibitor, glia-derived nexin, mouse contrapsin, ovalbumin, angiotensinogen, barley endosperm protein Z, and cowpox virus 38-kDa protein. Comparisons of the amino acid sequences of these individual serpins reveal a sequence identity of about 20–30%, with the greatest sequence conservation appearing at the COOH-terminal half of the proteins.

In contrast, much less is known about proteinase inhibitors from invertebrates. Most of the proteinase inhibitors isolated from invertebrates have been in the low $M_r$ range of about 5,000–15,000. A $M_r=155,000$ proteinase inhibitor has been isolated from crayfish plasma and an $\alpha_2$-macroglobulin-like proteinase inhibitor has been isolated from hemolymph of the American Lobster.

The only proteinase inhibitors isolated from invertebrates which are similar in size and characteristics to the serpins are a trypsin inhibitor ($M_r=42,000$) and a chymotrypsin inhibitor ($M_r=43,000$) which have been isolated from the hemolymph of the silkworm *Bombyx mori*. Sequences of the amino acids of these two silkworm proteinase inhibitors have revealed 56% amino acid identity with Manduca alaserpin (Takagi et al. (1990) J. Biochem. 108:372–378; Sasaki (1991) Eur. J. Biochem. 202:255).

In higher plants the natural repertoire of weapons available to fight insect predation are believed to include protease inhibitors (PIs). Known for some time (Reed and Haas, 1938 Cereal Chem. 15:59–68), diverse types of plant PIs are thought to provide protection to the tissues containing them (Richardson, 1977 Phytochemistry 16:159–169). Under certain conditions, insecticidal effects result from the addition of PIs to the artificial diets of insects (Steffens et al., 1978 J. Agar Food Chem. 26:170–176; Gatehouse et al., 1980 Phytochemistry 19:751–756; Broadway and Duffy, 1986a J. Insect Physiol. 32:827–833; Broadway and Duffy 1986b Entomologia Experimentalis et Applicata 41:33–38). Under field conditions, *Vigna unguiculata* (cowpea) varieties with high levels of trypsin inhibitor are more resistant to insect damage than varieties with low levels of the trypsin inhibitor (Gatehouse et al., 1980). In response to localized tissue injury, PI induction occurs on the wounded surface and continues through the remainder of the plant (Green and Ryan, 1972 Science 175:776–777).

The mechanism of PI action that accounts for insect toxicity cannot be easily explained. The inhibitor may arrest protein digestion, reducing essential amino acid levels and restricting insect growth and development. An important secondary effect caused by PIs may be the loss of valuable ions of the insect gut, in response to protease overproduction in the presence of PIs (Liener et al., 1980 *Toxic Constituents of Plant Foodstuffs* 2 edn., Academic Press, New York). Other environmental factors must also play a role in PI toxicity, as the inclusion of 10% cowpea trypsin inhibitor into artificial feeding tests are nontoxic (Pusztai et al., 1992 Brit. J. Nutrition 68:783–791). However, Boulter et al., EPA 0135343, published Mar. 27, 1985, reported that while cowpea PI was claimed to be effective when applied to edible plant parts, other trypsin inhibitors, e.g., those from soybean and lima bean, had no corresponding effect. The cDNA of this cowpea PI, a Bowman-Birk type inhibitor, was placed under the control of the 35S promoter of Cauliflower Mosaic virus (CaMV), and the 3' terminator of the nopaline synthase (Nos) gene. Cowpea PI was selected because it was previously known to have insecticidal activity. In numerous transgenic plants, the cowpea PI was expressed and accumulated anywhere from 0–1% of the total protein. Confirmation of PI production was via Western and enzyme activity assays. Bioassay of clones with first instar larvae of *H. virescens* were also conducted. In this case this trypsin inhibitor was effective in protecting against damaging insects. Insect survival was nearly 50% of the control (nontransformed) plant. (See also Hilder, V. A. et al. (1987) Nature 330:160–163.) Tomato inhibitor II (antitrypsin) also lowered the impact of predators on crop yield by decreasing the larval weight by as much as 15% (Johnson et al., 1989 Proc. Natl. Acad. Sci. USA 86:9871–9875). In the same study, however, tomato inhibitor I (a strong anti-chymotrypsin and weak anti-trypsin inhibitor) was ineffective in protecting against insect predation, and instead supported larval growth as well as did the control (nontransformed) plants.

Inhibitors of the Bowman-Birk type are relatively small (about 70 amino acids length) and multiply cross-linked with disulfite bridges. The Bowman-Birk inhibitors often display dual specificity, inhibiting, e.g., both trypsin and chymotrypsin. The inhibitors are found in many legume varieties. (See Ikenaka, T. and Norioka, S. (1986), in *Proteinase Inhibitors*, Barrett, A. J. and Salvesen, G. (eds.), Elsevier, Amsterdam, pp. 361–374).

No pattern has emerged to establish which inhibitors have a protective effect and which do not. Inhibitor specificity does not appear to be the only factor, since some trypsin inhibitor are effective while others are not. Little is known regarding the protective effects of chymotrypsin inhibitors or of elastase inhibitors. Inhibitors of the serpin superfamily have not previously been reported to have any protective effect in plants. Other factors affecting protection, such as pH optima and specific salt requirements, have not been systematically studied. Furthermore, experimental data over a range of test species is lacking. Protective effects have been demonstrated for only a few insect species.

Insect pests continue to cause significant crop losses each growing season. Although chemical insecticides are important for crop protection, concerns about toxicity and development of resistance among target populations have prompted a demand for alternative pest-control strategies. One such strategy is the use of insecticidal proteins, either applied on the plant surface or synthesized internally by plants genetically modified to express the protein. The toxins of various strains of *Bacillus thuringiensis* have been successfully employed, both topically and transgenically. Although protease PIs have been reported to protect plants against insect damage, both applied topically and expressed transgenically, the results have not been uniform, depending both on the target insect and on the specific PI employed. Nevertheless, certain PIs, such as the *M. sexta* serpin described herein, provide protection for certain crops and pests not otherwise controlled by prior art means.

The whitefly, *Bemisia tabaci*, has recently emerged as a major pest of vegetable crops and cotton in the far West and Southwest (see Henneberry, T. J. et al. (1992) "First Annual Review of the 5-year National Research and Action Plant for Development of Management and Control of the Sweet Potato Whitefly" USDA-ARS Bulletin. The insect is largely resistent to currently licensed insecticides. Various *B. thuringiensis* toxins are similarly ineffective, either as applied to plant surfaces or as transgenes. The whitefly feeds on phloem sap, whereas the *B. thuringiensis* toxin of transgenic plants is primarily intracellular.

SUMMARY OF THE INVENTION

The present invention presents the cDNA cloning and deduced amino acid sequence of a serpin from the insect *Manduca sexta*. The invention provides, for the first time, a serine proteinase inhibitor cloned from an insect. The serpin provides protection against insects that feed on plants, when applied to the plant or expressed as a transgene such that the serpin is ingested by insects as they feed on the plant. The cDNA has an open reading frame which codes for a 392-residue polypeptide of $M_r=43,500$, with a hydrophobic NH$_2$-terminal sequence which appears to be a signal peptide. The *M. sexta* serpin is believed to inhibit elastase due to the presence of alanine at the $P_1$ position of its reactive center and is, therefore, classified as an alaserpin. A glycoprotein of $M_r=47,000$, isolated from the hemolymph of *M. sexta* larvae has an identical NH$_2$-terminal sequence to that deduced from the alaserpin cDNA clone. This glycoprotein has been shown to inhibit porcine pancreatic elastase and bovine chymotrypsin. The cDNA clone may be modified by site directed mutagenesis to optimize specificity of the inhibitor for various serine proteases. Effective protection of alfalfa against thrips, of cotton against whitefly and of tobacco against *M. sexta* itself has been demonstrated.

BRIEF DESCRIPTION OF THE DRAWINGS

FIG. 3 is the cDNA (SEQ ID NO:1) and deduced amino acid sequence (SEQ ID NO:2) of *M. sexta* alaserpin.

DETAILED DESCRIPTION OF THE INVENTION

Figure 1:
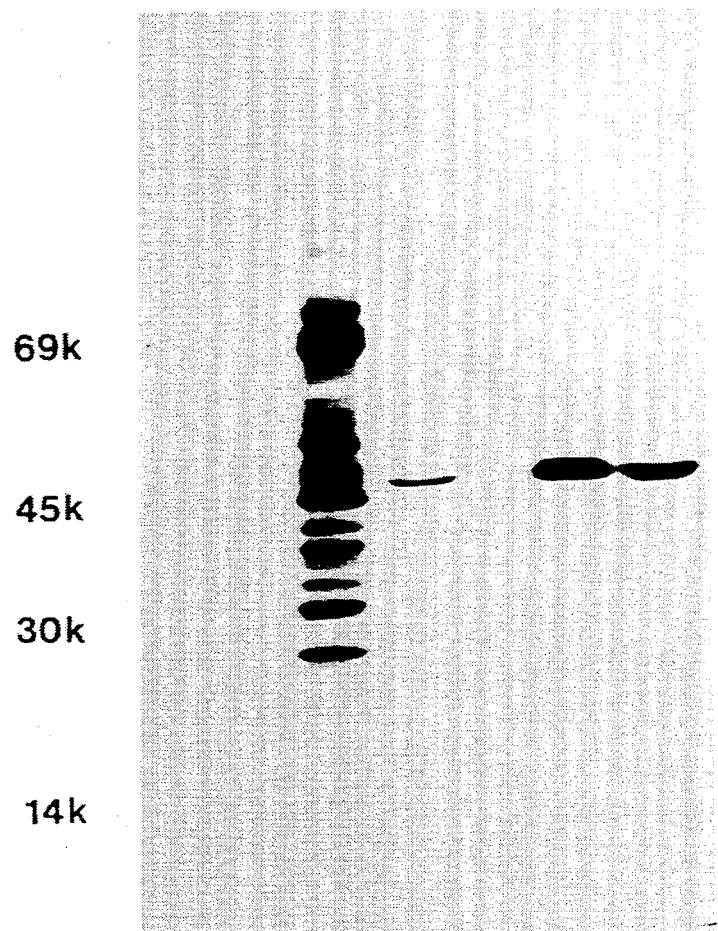
FIG. 1 is a SDS-polyacrylamide gel electrophoresis pattern of RNA translation products and immunoprecipitated proteins. Lane 1 represents protein standards; lane 2 represents translation products from polyadenylated RNA from body of day 2 fifth instar *M. sexta* larvae; lane 3 represents translation products precipitated by antiserum to apolipophorin-II; lane 4 represents translation products of RNA selected by hybridization with alaserpin cDNA; and lane 5 represents translation products of hybrid-selected RNA immunoprecipitates.

According to the present invention, cDNA and deduced amino acid sequences encoding all or part of a polypeptide sequence of a serine proteinase inhibitor from the insect *Manduca sexta* have been isolated, purified and characterized. The serpin is expressed in the fat body and the protein is secreted into the hemolymph.

The serine proteinase inhibitor cDNA was isolated from the fat body cDNA library. Total RNA from the fat body of *M. sexta* larvae was isolated and polyadenylated RNA was selected by passing the total RNA through an oligo-(dT)-cellulose column. The polyadenylated RNA was used to prepare cDNA and a cDNA library was constructed in λgt11 and screened with antiserum to *M. sexta* apolipophorin-II. Analysis of 12,000 recombinant plaques yielded two positive clones which were purified to homogeneity. The two positive clones were digested to reveal inserts of approximately 1.3 and 1.4 kilobases, which were subcloned for sequence analysis. The polyadenylated RNA was hybridized with the cDNA insert and hybrid selected RNA translated in vitro. The translation products and proteins were examined by SDS-PAGE. The 1.4 kilobase insert was used to generate unidirectional deletion clones which were, in turn, used for sequencing.

Sequencing of the serpin cDNA revealed a sequence identity of the deduced amino acid sequence with that of elastase inhibitor, and it is believed, therefore, that the *M. sexta* serpin is elastase specific. Additionally, alignment of the *M. sexta* alaserpin protein sequence with other members of the serpin superfamily reveals between 15 and 30% homology.

To be used as a plant protectant, the *M. sexta* serpin should be present on or in the tissues of the plant so as to contact the insect as it feeds on the plant. Any method suitable to achieve that result can be used, including applying the PI to the surface of the plant or by expressing the PI as a transgene in plant cells. The former can be accomplished by known techniques for the external application of materials to plants, notably by spraying. Since such techniques are well-known and fully disclosed elsewhere for cowpea PI (see Boulton et al., supra) extensive teaching of suitable techniques are not repeated herein. It will be understood that the proteinaceous nature of the PI necessitates precautions to ensure stability, e.g., avoidance of high temperatures (>50° C.), acids, bases, organic solvents, strong detergents, violent agitation and the like, as is well-known in the art.

Certain basic principles for effective expression of a transgene in plants are well understood in the art. Regulated expression is accomplished by proper choice of a plant expressible promoter combined with the PI coding sequence. A wide variety of suitable plant-expressible promoters are known, including promoters of other plant genes, plant virus promoters, T-DNA promoters of *Agrobacterium tumefaciens* and *Agrobacterium rhizogenes*, and various procaryotic promoters. The techniques for constructing a functional chimeric gene having a coding region and a ]promoter obtained from different sources are well-known. Suitable plant promoters can be those which result in constitutive expression, such as the promoters of PEP carboxylase or ubiquitin (Cushman, J. C. et al. (1983) Plant Mol. Biol., in press; Christensen and Quail (1989) Plant Mol. Biol. 12:619–632), light regulated expression, such as chlorophyll AB binding protein (Castresana, C. et al. (1988) EMBO J. 7:1929–1936), or the small subunit of ribulose bisphosphate carboxylase, tissue-specific or development stage-specific regulation such as phaseolin (Bustos, M. M. et al. (1991) EMBO J. 10:1469–1479), or self-incompatibility genes (Clarke, A. et al., U.S. Pat. No. 5,053,331), or environmentally-regulated promoters such as heat shock (Czarnecka, E. et al. (1989) Mol. Cell. Biol. 9:3457–3463), or alcohol dehydrogenase (Walker, J. C. et al. (1987) Proc. Natl. Acad. Sci. USA 84:6624–6628). Viral promoters and T-DNA promoters are typically constitutive promoters that drive high expression levels. Well-known promoters in this category include the 35S promoter of cauliflower mosaic virus (Benfey, P. N. et al. (1989) EMBO J. 8:2193–2202) and the various opine synthase promoters of T-DNA (Gelvin, S. B., U.S. Pat. No. 4,771,002). Any promoter capable of functioning in a plant cell can be used in combination with the disclosed PI coding sequences. The choice of promoter will be based on considerations of the insect pest to be controlled, including its feeding habits, timing of predation, life stage of greatest sensitivity to PI and the amount of PI needed to provide a desired protection level.

As with promoters, the choice of polyadenylation signal sequence to be linked to the 3'-end of the PI coding region is a matter of choice from among a large variety of known poly-A signal sequences, from a variety of plant, viral and Agrobacterium sources. Those of the CaMV 19S and 35S genes have been employed herein, but any polyA signal sequence functional in plant cells can be used.

Transformation of plant cells can be accomplished by many techniques known in the art. A powerful set of techniques has been provided by the development of the Ti plasmid system of Agrobacterium species (An, G. et al. (1988) In: Plant Mol. Biol. Manual A3:1–19, Kluwer Academic Publishers, Dordrecht; Rogers, S. G. et al. (1988) in *Methods for Plant Molecular Biology*, Weissbach, A. and Weissbach, H. (eds.) pp. 423–436); Grierson, D. and Covey, S. N. (1988) *Plant Molecular Biology* 2nd Ed., Blackie and Son Ltd., Glasgow; Horsch, R. B. et al. (1988) In: Plant Mol. Biol. Manual A5:1–9). Ballistic transformation, using microscopic particles coated with the DNA to be introduced, has been effectively applied to a wide variety of plant species. (Tomes, D. T. et al. (1990) In: Plant Mol. Biol. Manual A13:1–22.) Other methods, such as direct protoplast transformation with DNA (Paszkowski, J. and Saul, M. W. (1988) in *Methods for Plant Molecular Biology*, Weissbach, A. and Weissbach, H. (eds.), pp. 447–463) and use of viral vectors (Ahlquist, P. G., U.S. Pat. No. 4,885,248; Brisson, N. and Hohn, T. (1988) in *Methods for Plant Molecular Biology*, Weissbach, A. and Weissbach, H. (eds.), pp. 437–446) are effective under certain circumstances. Virtually every plant of commercial value has been successfully transformed. Those skilled in the art are able to choose and employ the established methods of transformation suitable to obtain regenerable transformed plant cells or protoplasts.

The detection of transformed cells can be carried out by a direct assay for expression of the transgene, or by use of a selectable marker co-transformed with the desired PI transgene. A frequently employed selectable marker is the neomycin phosphotransferase II gene (NPTII) which confers kanamycin resistance to transformed cells. Detection of transformed cells can also be achieved by a readily detectable co-transgene, for example, $\beta$-glucuronidase (GUS) or luciferase (Grierson and Covey, supra).

Regeneration of whole plants from transformed cells or from transformed protoplasts is achieved by a variety of known techniques. The protocols vary according to the plant species and the type of transformed cell or protoplast available as the starting point. Protocols are known for regenerating virtually any crop species or ornamental species.

For general reviews see, e.g., Tisserat, B. (1985) in *Plant Cell Culture a Practical Approach*, Dixon, R. A. (ed.), IRL Press, Oxford, pp. 79–105; Horsch, R. B. et al. (1988) supra. Transformable and regenerable crop species include all major crops grown in the U.S.: soybean, corn, wheat, barley, sorghum, cotton, alfalfa, tomato, potato, the Brassica vegetables, carrot, bean, pea, citrus, grape, tobacco and many pine species. It is well understood in the art that various cultivars within a species may require optimization of process variables to achieve most efficient regeneration. Such optimization is well within the ability of those skilled in the art to accomplish without undue experimentation.

Protection against insect damage can be obtained by various modes of action. Toxicity to the insect is but one means of achieving protection. Other means include, but are not limited to, anti-feedant activity, aversive effects, inhibition of growth or metamorphosis, interference with reproductive capacity and production of sublethal harm that renders the insect more susceptible to other environmental or chemical stresses. Therefore, any effect which can be associated with a reduction in insect-induced plant damage is deemed a protective effect. Protection is measured by quantifying effects observed on a target insect upon exposure to the protective agent. Such effects include, but are not limited to, cessation of feeding, reduced growth rate, reduced emergence of pupae from egg cases, and insect (or larval) death. Alternatively, direct measurement of plant damage can be quantified, for example, by assessing leaf damage or measuring crop yields. A "plant protective amount" of a protectant, in this case a PI, is that amount which results in a measurable protective effect of sufficient magnitude to be statistically significant when compared with a control where no protectant is present. It will be understood that insect bioassays are difficult to perform with consistent results. Negative results (no observed protective effect) do not necessarily mean that no protective effect exists, but may only mean that the effect is only observable under different experimental conditions, for example, at a different life-stage or a different physiological condition of the insect (or plant), or under different environmental conditions (soil type, temperature, humidity, etc). A positive result (protection effect observed) can be considered meaningful provided the controls are run under comparable conditions.

Insects can be expected to show differing degrees of susceptibility to a given protective agent. It will be understood that where a protective effect has been observed with a given insect, an effect will be expected for other insects which belong to the same genus and feed in a manner similar to the tested insect species. The observed effect can also be generalized to other plants on which the test insect species feeds. Thus, for example, observed protective effects against whitefly on tobacco can be generalized to whitefly in other crops as well.

The following examples are provided in order to further describe the invention and provide details of the *M. sexta* PI and its use in protecting plants against insect damage. Abbreviations used are those commonly accepted by major journals such as those cited herein. Specific techniques not described in detail are more fully published elsewhere, for example, see Sambrook, J. et al. (1989) *Molecular Cloning, a Laboratory Manual*, Cold Spring Harbor Laboratory Press, Plainview, N.Y.; and *Methods for Plant Molecular Biology* (1988) Weissbach, A. and Weissbach, H. (eds.), Academic Press, San Diego; as well as other volumes of the extensive Methods in Enzymology series also published by Academic Press. See also, various volumes of *Plant Mol. Biol. Manual*, published by Kluwer Academic Publisher, Dordrecht.

EXAMPLES

EXAMPLE I

A. Isolation, cDNA Library Construction and Screening

*M. sexta* eggs were obtained and larvae were reared from the eggs. Total RNA was isolated from the fat body of day 2 fifth instar male larvae and polyadenylated RNA was selected by passing twice through an oligo(dT)-cellulose column. Five $\mu$g of polyadenylated RNA was used to prepare cDNA using a commercial kit (Amersham Corp.). A cDNA library was constructed in $\lambda$gt11 and screened with antiserum to *M. sexta* apolipophorin-II. (See, e.g., Shapiro, J. P. et al. (1984) J. Biol. Chem. 259:3680–3685). Analysis of 12,000 recombinant plaques yielded two positive clones which were purified to homogeneity. Digestion of these two clones with EcoRI revealed inserts of approximately 1.3 and 1.4 kb. The 1.4 kb insert was subcloned into pUC8 and then into M13-mp18 for sequence analysis. RNA was fractionated in formaldehyde gels and transferred to nitrocellulose. Hybridizations with the cDNA insert labeled with $^{32}$P by nick translation were performed.

Hybrid Select Translation

Hybrid selection was then carried out. Five $\mu$g plasmid DNA containing the 1.4 kb insert was linearized with EcoRI and spotted onto a dry 1-cm$^2$ nitrocellulose filter. The DNA was denatured on 0.5N NaOH, 1.5M NaCl, neutralized in 2M Tris pH 7.4, and 2$\times$SSC and baked for 2 hours at 80° C. under vacuum. The filter was incubated for 30 min. at 42° C. in hybridization buffer (50% formamide, 750 mM NaCl, 40 mM Pipes, pH 6.4, 0.2% SDS and 5 mM EDTA) and then in 30 $\mu$l of hybridization buffer containing 150 $\mu$g/ml of polyadenylated RNA for 4 hours at 42° C. The filter was then washed twice with 1 ml of hybridization buffer at 42° C.; once with 1 ml of the wash buffer (150 mM NaCl, 40 mM Pipes, pH 6.4, 0.2% SDS and 5 mM EDTA) at 42° C. eight times with 1 ml of the wash buffer at 60° C.; and twice with 1 ml of 2 mM EDTA at 60° C. The hybridized RNA was eluted by boiling the filter for 1 min. in 200$\mu$l of 1 mM EDTA, pH 7.9, containing 5 $\mu$g of tRNA and quick freezing in a dry ice/ethanol bath. The solution was allowed to thaw on ice, and RNA was then precipitated with ethanol and dissolved in 10 $\mu$l of water. The RNA was translated in vitro using rabbit reticulocyte lysate (Promega) and [$^{35}$S] methionine as described in the protocol supplied with the kit. Total translation products and immunoprecipitated proteins were examined by SDS-PAGE carried out in a 10% acrylamide gel and subjected to fluorography.

EXAMPLE 2

The 1.4 kb EcoRI insert subcloned into M13-mp18 in both orientations was used to generate unidirectional deletion clones by exonuclease III. (See, e.g., Henikoff, S. (1984) Gene (Amst.), 28:351–359.) Single-stranded DNA was sequenced by the dideoxy chain termination method. (See, e.g., Sanger, F. (1977) Proc. Natl. Acad. Sci. USA 74:5463–5467.)

EXAMPLE 3

The National Biomedical Research Foundation protein sequence data was searched with the FASTP program, and the significance of similarity of the sequences was determined with the RDF program. (see, Lipman, D. J. et al. (1985) Science 227:1435–1441.) Progressive sequence alignment and construction of phylogenetic trees were performed with the computer programs of Feng and Doolittle (See, Feng, D. F. and Doolittle, D. F. (1987) J. Mol. Evol. 25:351–360). Serpin sequences were obtained from human $\alpha_1$-antitrypsin, antithrombin, chicken ovalbumin, gene-Y ovalbumin-related protein, $\alpha_2$-antiplasmin, rat angiotensinogen, $\alpha_1$-antichymotrypsin, human glia-derived nexin, endothelial cell-type plasminogen activator inhibitor, protein C inhibitor and cowpox virus hemorrhage-specific protein.

EXAMPLE 4

A. Purification of a Hemolymph Elastase Inhibitor

Hemolymph from day 3 fifth instar larvae (20 ml) was collected into 5 ml of cold 0.1M sodium phosphate, pH 7.0, 10 mM glutathione, 1 mM diisopropyl fluorophosphate. Hemocytes were removed by centrifugation, and the supernatant was dialyzed against 20 mM ammonium acetate, pH 6.0. A precipitate was removed by centrifugation (5000$\times$g, 10 min.), and the supernatant was applied to a column of DEAE-Bio-Gel (1$\times$20 cm) equilibrated with 20 mM ammonium acetate, pH 6.0. The column was eluted with 100 ml of the starting buffer and then with a gradient of 0–200 mM NaCl in starting buffer (300 ml total). Five-ml fractions were collected at 1 ml/min. Proteinase inhibitor activity was assayed by mixing 10µl samples from column fractions with 1 µg porcine pancreatic elastase and residual activity assayed by placing the reaction mixture in a well cut into an agarose gel containing casein (protease substrate gel tablets, Bio-Rad). After 16 hours clear circles around the wells were measured, and protease activity was expressed as the area of the gel in which casein was hydrolyzed. For calculations of total activity, 1 unit was defined as the amount of sample required to give 50% inhibition of 1 µg of elastase. Fractions 57-59, which contained elastase inhibitory activity, were pooled and applied to a column of Sephacryl S-200 (90×1 cm), which was eluted with 20 mM ammonium acetate, pH 6.7. Five-ml fractions were collected at 0.3 ml/min. Fractions were assayed for anti-elastase activity as described above. Fractions 20-23, corresponding to a peak of elastase inhibitory activity, were pooled.

B. Analysis of Manduca Elastase Inhibitor

Steps during the purification were analyzed for anti-elastase and the molecular weight of the hemolymph elastase inhibitor was determined by SDS-PAGE carried out in a 5-15% acrylamide gradient gel and stained with Coomassie Blue. The $NH_2$-terminal amino acid sequence was determined. The carbohydrate content was determined by the phenol/sulfuric acid method. Protein-bound carbohydrate was further analyzed by staining SDS-polyacrylamide gels with fluorescein isothiocyanate-conjugated concanavalin A (Sigma). The isoelectric point of the protein was estimated by isoelectric focusing in a pH 3-9 gel (Phast System,, Pharmacia LKB Biotechnology, Inc.). Antiserum was produced in New Zealand White rabbits by intramuscular injection of 100 µg of elastase inhibitor in Freund's complete adjuvant followed after six weeks by injection of 100 µg of elastase inhibitor in Freund's incomplete adjuvant. Blood was collected after two weeks, and serum was stored at −70° C. The antiserum was characterized by Western blot analysis of hemolymph proteins and found to be specific for the 47,000 dalton elastase inhibitor.

Association constants for the purified hemolymph proteinase inhibitor and various serine proteinases were determined under second order conditions. Bovine trypsin and chymotrypsin and porcine pancreatic elastase were obtained from Sigma. After allowing equimolar concentrations of enzyme and inhibitor to react for various periods of time, residual enzyme activity was measured at 25° C. in 0.1 mM Tris-HCl, pH 8.0, using 0.5 mM N-succinyl-L-alanyl-L-alanyl-L-prolyl-L-leucyl-p-nitroanalide (Sigma) as a substrate for elastase, 0.1 mM N-succinyl-L-alanyl-L-alanyl-L-prolyl-L phenylalanyl-p-nitroanalide as a substrate for chymotrypsin, and 0.5 mM N-benzoyl-L-arginyl-ethyl ester (Sigma) as a substrate for trypsin.

It should be readily apparent from the foregoing illustrative examples that numerous potential products are provided by the present invention. The polypeptide provided by this invention may be useful in various expression systems and products or in synthetic products, the structure of which was first made known by the present invention.

Turning now to the accompanying figures, the results of the foregoing examples are shown. After screening the M. sexta fat body cDNA library with antiserum thought to be specific for apolipophorin-II, as described in Example 1, two clones were isolated that hybridized to a fat body RNA of 1470 nucleotides. This fat body RNA was too small to encode apolipophorin-II ($M_r$=78,000). The clone containing the 1.4 kb insert was used to identify a protein product of the corresponding mRNA by hybrid select translation. FIG. 1 illustrates the SDS-PAGE staining pattern of the total translation products (1 and 3), the RNA translation products selected by hybridization with alaserpin cDNA (lane 4) and immunoprecipitated translation products of hybrid select RNA (lane 5); all having a $M_r$ equal to about 46,000 daltons.

Figure 2:
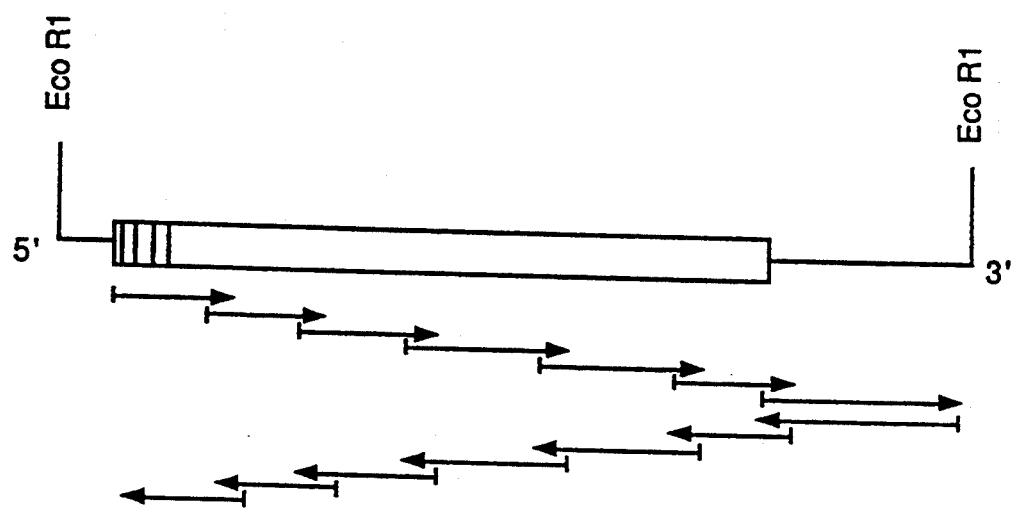
FIG. 2 is a diagrammatic representation of the sequencing strategy for *M. sexta* alaserpin cDNA.

To learn more about this 46,000 dalton protein, the 1.4 kb cDNA clone was sequenced as described in Example 2. The strategy for sequencing is shown in FIG. 2 and the nucleotide and deduced amino acid sequences are shown in FIG. 3. In FIG. 2 the box indicates the sequence coding for the protein and the shaded area adjacent to the 5' end indicates the sequence coding for the signal peptide. Arrows indicate the direction and extent of each sequence determination. In FIG. 3 the amino acids in the mature hemolymph protein are assigned positive numbers, those in the putative signal peptide are assigned negative numbers.

Amino acids which are underlined were confirmed by protein sequencing. The 1427-base pair cDNA sequence contains an open reading frame beginning with an ATG codon at position 25 and extends to position 1200, followed by a 227 base pair 3'-untranslated sequence. While this clone does not contain a poly(A) tail, a consensus polyadenylation signal, AATAAA, is present beginning at position 1414. The 5 nucleotides upstream from the ATG codon are GCAAC, which match in three positions with a consensus sequence for eukaryotic initiation sites, including the highly conserved purine at position −3.

As described in Example 3, sequence alignment of the M. sexta protein with other members of the serpin superfamily of proteinase inhibitors demonstrated sequence similarities ranging from about 31.7% identical residues when compared with human plasminogen activator inhibitor, to about 15.8% identity with rat angiotensinogen. Identical residues appear throughout the sequences, with greater similarity in the COOH-terminal halves of the proteins. The same amino acid is present in fifteen positions in all sequences and another 41 positions with identical amino acids in at least nine of the twelve proteins. These data support the conclusion that the M. sexta cDNA codes for a member of the serpin superfamily.

The sequence alignments also permit a prediction of the location of the reactive center of the M. sexta protein. The $P_1$ residue of the reactive center, which determines inhibitor specificity, is predicted to be alanine at position 343 of the mature protein. According to the serpin classifications of Carrell, R. et al (1985) Trends Biochem. Sci. 10:20-24, which classifies setpins according to their reactive center, the M. sexta protein is an alaserpin, and its specificity should be toward proteinases, such as elastase, which cleave at alanine. Table 1, modified from Carrell et al., presents a comparison of the predicted reactive center of the M. sexta serpin with those of known vertebrate serpins.

TABLE 1

| Inhibitor | Target | Reactive center residues | | | | | |
|---|---|---|---|---|---|---|---|
| | | $P_2$ | $P_1$ | $P_1'$ | $P_2'$ | $P_3'$ | $P_4'$ |
| $\alpha_1$-Antitrypsin | Elastase | Pro | Met | Ser | Ile | Pro | Pro* |
| $\alpha_1$-Anti- | Chymase | Leu | Leu | Ser | Ala | Leu | Val* |

TABLE 1-continued

| Inhibitor | Target | Reactive center residues | | | | | |
|---|---|---|---|---|---|---|---|
| | | $P_2$ | $P_1$ | $P_1'$ | $P_2'$ | $P_3'$ | $P_4'$ |
| chymotrypsin | | | | | | | |
| Anti-thrombin-III | Thrombin | Gly | Arg | Ser | Leu | Asn | Pro* |
| Mouse contrapsin | "Trypsin" | Arg | Lys | Ala | Ile | Leu | Pro* |
| Ovalbumin | ?Elastase | Ala | Ala | Ser | Val | Ser | Glu* |
| M. sexta alaserpin | ?Elastase | Pro | Ala | Ser | Leu | Ile | Leu* |

*SEQ ID NOs: 3–8 are the target sequences of $\alpha_1$-antitrypsin, $\alpha_1$-antichymotrypsin, antithrombin-III, mouse contrapsin, ovalbumin and M. sexta alaserpin, respectively.

Figure 4:
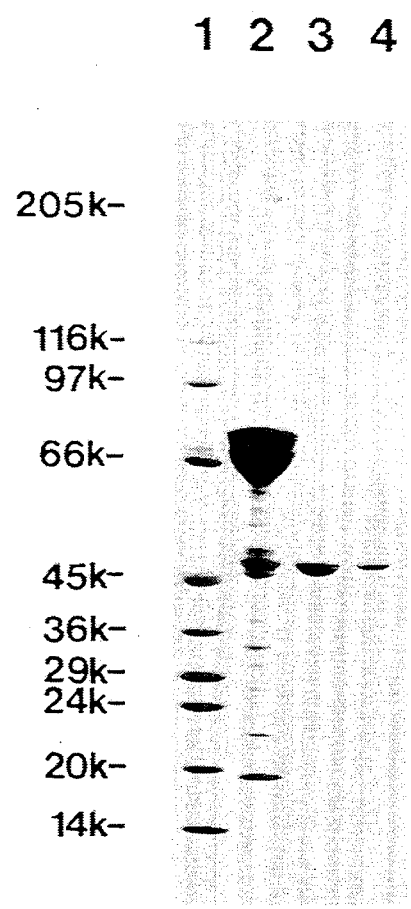
FIG. 4 is a SDS-PAGE staining pattern of *M. sexta* alaserpin at different stages of purification. Lane 1 represents protein standards; lane 2 represents hemolymph from day 3 fifth instar *M. sexta* larvae; lane 3 represents alaserpin after ion-exchange chromatography; lane 4 represents alaserpin after gel filtration.

Having determined the predicted size, amino acid composition, and proteinase specificity of the M. sexta alaserpin, isolation and purification of the hemolymph elastase inhibitor was conducted. Example 4 describes the isolation and purification procedures. FIG. 4 shows SDS-PAGE staining patterns of M. sexta alaserpin at different stages of purification, wherein lane 2 corresponds to the hemolymph from day 3 fifth instar larvae and shows numerous protein bands with broad staining bands centered around 66 and 46 kDa, lane 3 represents the hemolymph elastase inhibitor after ion-exchange chromatography on DEAE-Bio-Gel which separated the elastase inhibitor from the majority of other hemolymph proteins, and lane 4 represents the elastase inhibitor after gel filtration on Sephacryl S-200. Table 2 summarizes the results of the isolation procedure.

TABLE 2

| Step | Total Volume ml | Total Activity units | Total Protein mg | Specific Activity units/mg | Yield % | Purification -fold |
|---|---|---|---|---|---|---|
| Hemolymph | 20 | 28,000 | 340 | 82 | | |
| DEAE | 15 | 24,000 | 5.6 | 4,286 | 86 | 52 |
| Sephacryl | 18 | 6,920 | 1.17 | 5,915 | 25 | 72 |

Finally, elastase specificity of the M. sexta alaserpin was determined by measuring the association rate constants ($k_{assoc}$) for the inhibitor with porcine pancreatic elastase, bovine chymotrypsin and bovine trypsin. The M. sexta alaserpin had a $k_{assoc}$ of $1 \times 10^7$ $M^{-1}$ $s^{-1}$ for elastase, $7 \times 10^4$ $M^{-1}$ $s^{-1}$ for chymotrypsin, and $5 \times 10^2$ $M^{-1}$ $s^1$ for trypsin. These results were consistent with the predicted specificity from the sequence at the active center of the inhibitor.

Thus, the present invention presents, for the first time, the isolated and characterized cDNA and protein for a serine proteinase inhibitor which is a member of the serpin superfamily from the insect M. sexta. The gene is expressed in the fat body and the protein is secreted into the hemolymph. The purified M. sexta serpin has been determined to be specific for elastase.

The full extent to which the DNA sequence of the present invention will have use in various alternative methods of protein synthesis or expression systems in transgenic insects or other species cannot yet be determined. Viewed in this light, therefore, the specific disclosures of the illustrative examples are not intended to be limiting upon the scope of the present invention and numerous modifications and variations are expected to occur to those skilled in the art. As one example, while the DNA sequence provided by the examples includes cDNA and genomic DNA sequences, because this application provides amino acid sequence information essential to manufacture of DNA sequences, the invention also comprehends such manufactured DNA sequences as may be constructed based upon knowledge of the DNA sequences of the serpin superfamily. These may code for the M. sexta alaserpin, as well as for fragments thereof and serpin analogs which may share one or more biological properties of naturally-occurring serine proteinase inhibitors, but not share others.

The DNA sequence provided by the present invention is therefore seen to comprehend all DNA sequences suitable for use in securing procaryotic or eucaryotic expression of a polypeptide product having at least a part of the primary structural conformation and one or more of the biological properties of M. sexta alaserpin.

EXAMPLE 5

Figure 5:
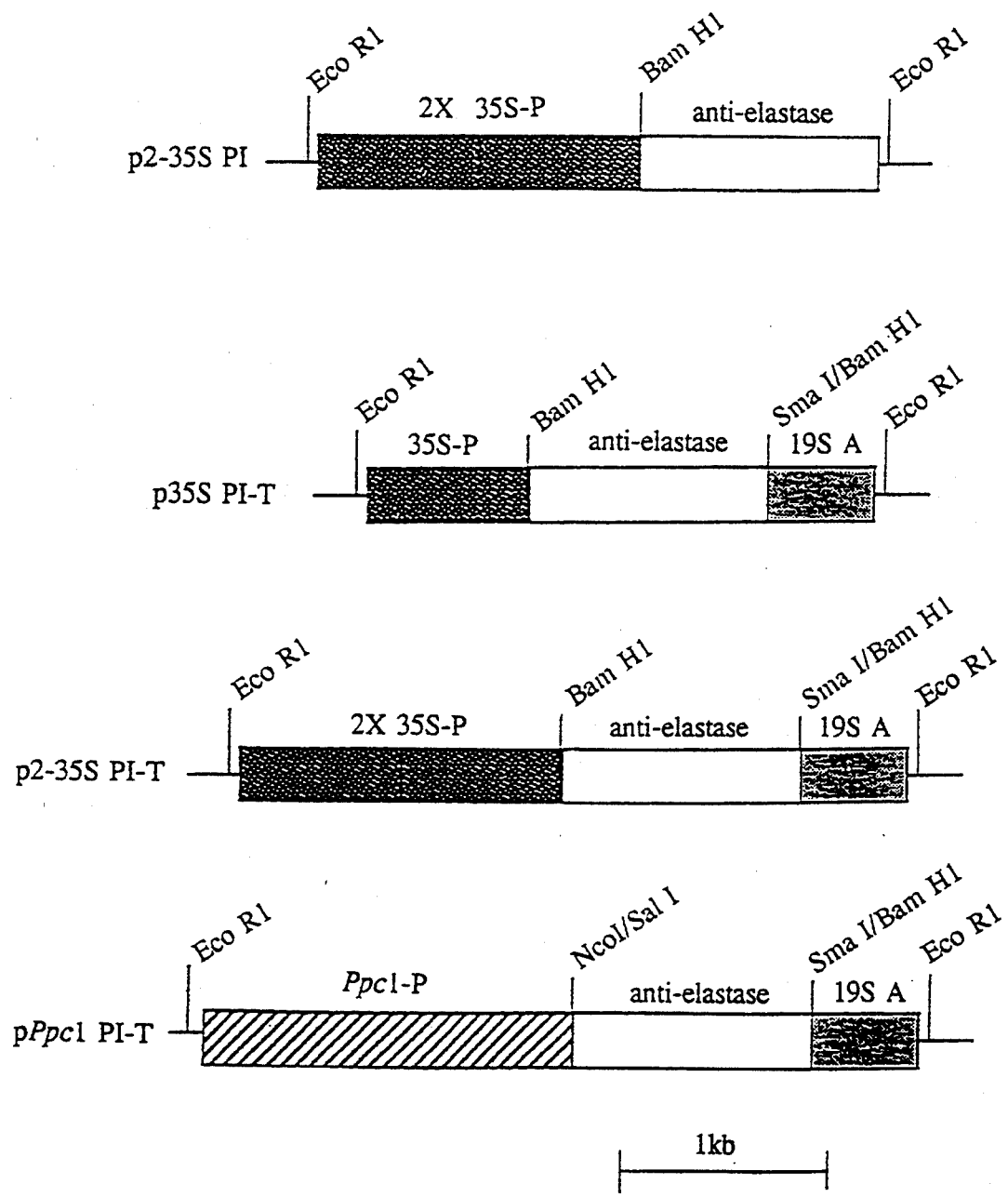
FIG. 5 is a diagram of plasmid constructions containing the anti-elastase proteinase inhibitor of *M. sexta*. Strategic restriction sites are depicted.

Isolation of a cDNA encoding the anti-elastase (PI) found in serum of Manduca sexta has been described (Kanost et al., 1989). Plasmids used in vector construction were of the pUC or pBS (Stratagene) type. The CaMV 35S promoter, the double enhancer 35S ]promoter, and the phosphoenolpyruvate carboxylase promoter (Ppc1 promoter) from Mesembryanthemum crystallinum (Cushman et al., 1989) were inserted 5' of the anti-elastase cDNA clone using standard molecular methods. Following 19S terminator assembly 3' of the cDNA, the constructs were excised as a single EcoRI fragment and inserted into pAN 70. These constructs, p35SPI-T, p2-35SPI, p2-35SPI-T are shown in FIG. 5. After transformation into E. coli DH5α, transformants were selected on 10 μg/ml tetracycline. Plasmid DNA from individual colonies was isolated, digested with EcoRI, and southern analysis done to confirm the plasmid construction following tri-parental mating.

EXAMPLE 6

Modification of PI inhibitor specificity. Modified PI gene constructs fox high level expression are diagrammed in FIG. 6.

The specificity of serpins for inhibition of different serine proteinases is primarily dependent on the amino acid residue at the. P1 position of the reactive site. Manduca sexta alaserpin has alanine at its P1 position, determining its specificity for inhibition of elastase, which cleaves at alanine residues. Site directed mutagenesis of the alaserpin cDNA was performed to change the amino acid encoded at the P1 position to phenylalanine (Ala343Phe), which is expected to result in specificity for inhibition of chymotrypsin, or to lysine (Ala343Lsy), which is expected to result in specificity for inhibition of trypsin. Mutagenesis was carried out by the method described by Hemsley et al. (1989) Nucl. Acids Res. 17:6545). The different oligonucleotides used to produce mutations in the codon for the P1 residue are shown below.

|            |     |     |     |     | P1  |     |     |     |                   |
|------------|-----|-----|-----|-----|-----|-----|-----|-----|-------------------|
| Alaserpin  | GGT | ATC | GTA | CCG | GCG | AGT | TTG | ATA | CTA (SEQ ID NO: 9) |
|            | Gly | Ile | Val | Pro | Ala | Ser | Leu | Ile | Leu (SEQ ID NO: 10) |
| mutagenesis primers: | GGT | ATC | GTA | CCG | TTT | AGT | TTG | ATA | CTA (SEQ ID NO: 11) |
| Phe mutant | Gly | Ile | Val | Pro | Phe | Ser | Leu | Ile | Leu (SEQ ID NO: 12) |
| Lys mutant | GGT | ATC | GTA | CCG | AAG | AGT | TTG | ATA | CT (SEQ ID NO: 13) |
|            | Gly | Ile | Val | Pro | Lys | Ser | Leu | Ile | Leu (SEQ ID NO: 14) |

The oligonucleotide-directed mutations were verified by DNA sequencing of the relevant regions of the resulting plasmids carrying the mutant serpin cDNAs.

EXAMPLE 7

Protective effect on thrips predation of alfalfa. Initial experiments focused on the identification of alfalfa plants with high regeneration efficiency via somatic embryogenesis. A minimum of 50 plants were tested for regeneration potential: Regen-S germplasm (Bingham et al, 1975) and potential parent clones in varietal development (Vista, Woodland, Calif.): variety Moapa 69 and Cuf-101. Using standard tissue culture regeneration protocols (McCoy and Bingham, 1977) we identified over 50 plants (predominately from Regen-S) that regenerated. Within these 50 plants, we identified one plant, V-154, that was easily and efficiently transformed and regenerated at a high frequency. For all subsequent experiments, V-154 was employed.

PI Gene Constructs for Plant Expression

The techniques used to construct plant expression cassettes of the *M. sexta* PI were generally standard methods for aligning desired DNA fragments in desired position and orientation with respect to one another. The steps employed to express the PI under control of either a single 35 promoter or tandem 35S promoters (2×35) and 19S terminator are described as follows.

The TPSSNPTII fusion in pSP18 was a pea small subunit transit peptide sequence arranged 5' of the NPT II gene for study in chloroplast import. This construct is described in: Wasmann, C. C. et al. (1986) Mol. Gen. Genet. 205:446–453. This clone was designated as 6-16-85 #14. TPSSNPTII was cut with BamH1, then treated with klenow fragment of DNA polymerase and dNTPS to destroy the BAM site in the polylinker of pSP18. Resulting plasmid name: 6-10-88#1. 6-10-88 was cut with HindIII endonuclease and filled in with Klenow fragment polymerase. Phosphorylated Bam H1 linkers were ligated into the former HindIII site, then precipitated, then cut with BamH1. Following ligation the plasmid was designated 6-15-88 #3.

The ALA-serpin and anti-elastase was provided as an EcoR1, EcoR1, insert in pUC8. At the initiator ATG of the alaserpin gene, NcoI endonuclease digestion and klenow treatment was followed by an EcoR1 endonuclease digestion and the entire ALA-serpin fragment isolated. (6-15-88 #3) was digested with EcoRV and EcoR1 endonucleases, leaving the ATG in the SSU transit peptide intact, also leaving a 5 amino acid leader from the transit peptide, and creating a Bcl site. Religation resulted in a fusion CTATGATCATG (SEQ ID NO:15). The resulting plasmid was known as 6-20-88 #1.

pUC18 was digested with EcoR1 for preparation as an assembly vector. A 35S promoter construct in pUC 19 was cut with EcoR1 and BamHI endonucleases and the promoter liberated. Plasmid 6-20-88 #1 was cut with BamH1 and Sal endonucleases and a 590 bp fragment isolated. The original Kanost ALA-serpin was digested with EcoR1 and Sal endonucleases and an 800 bp band isolated. In one ligation, the RI-digested pUC18 was combined with the double 35S promoter (590 bp) EcoRI/BamHI, the BamHI/Sal restricted 6-20-88, and the Sal/EcoR1 (800 bp) digested ALA-serpin coding segment to yield a plasmid designated 7-2-88. The promoter ALA-serpin combined construct was removed from 7-2-88 with EcoR1 endonuclease, inserted into pAN70 (From Dr. Jeff Velton, New Mexico State) and subsequently introduced into *Agrobacterium tumefaciens* LBA4404 with the use of the helper plasmid pRK2013.

19S Terminator pJIT117 (Guerineau, F. et al. (1988) Nucl. Acids Res. 16:11380) was digested with EcoR1 endonuclease and filled in to destroy the RI site. The resulting plasmid was designated 6-5-89 #1-1.

Single 35S Assembly

Plasmid 6-5-89 #1-1 was cut with BamH1 and KpnI endonucleases and the released 19S polyA site was inserted into identical sites in pSP18. The result, designated as 6-22-89 #1, contained the 19S terminator of the CaMV virus. Plasmid 6-22-89 #1 was next digested with BamHI and Sma endonucleases and the 3' side of the ALA-serpin was inserted and ligated to form 6-29-89 #1-1. A single 35S promoter was from pBI121.1 (Clonetech). The single 35S promoter was digested with BamH1 and HindIII endonucleases and the 5' fragment inserted into pSP18 making plasmid 1-31-89 #1. Next plasmid 7-2-88 #1 (5' Alaserpin) isolated as a Hind Bam fragment was cloned downstream of the promoter in identical sites, producing plasmid 4-24-89 #13. The Alaserpin clone in pUC8 was digested with HindIII and EcoR1 endonucleases and the 3' side of the alaserpin coding sequence was inserted into pSP18 (MAP 116), designated 12-6-88 1-1.

Plasmid 12-6-88 1-1 was cut with BalI digestion, treated with klenow and then cut with EcoRI endonuclease. Plasmid 10-6-88 #1-1, having a Nos terminator of nopaline synthase, was cut with BamHI endonuclease, treated with klenow and then cut with EcoR1 endonuclease. The isolated fragment was inserted into opened 12-6-88 1-1, giving a plasmid designated 4-18-89 #6 (3' ALA-serpin+NOS ter).

Plasmid 6-5-89 #1-1 has the 3' end of the ALAserpin coding region as a HindIII/EcoR1 segment cloned in to pSP18. Acting as the vector plasmid, 6-22-89 #1-1 was cut with Sma and HindIII endonucleases. Also plasmid 4-18-89 #6 was digested with Bam, endonuclease, then klenow, then HindIII endonuclease to isolate a 270 bp fragment which was inserted into opened 6-22-89 #101 to form plasmid 6-29-89 #1. Next, plasmid 6-29-89 #1 was digested with HindIII and EcoR1 endonucleases, plasmid 4-24-89 #13 was cut with HindIII and BglI endonucleases (5' ALA-serpin) and pSP18 was cut with BglI and EcoRI endonucleases. Following ligation, plasmid 7-12-89- #3-4 was formed, carrying the nonduplicated 35S promoter, complete alaserpin gene and 19S terminator.

To make double 35S with terminator:

Plasmid 6-29-89 #1-1 was cut with HindIII and EcoR1 endonucleases, the ALA-serpin construct in pUC18 was cut with Pst and HindIII endonucleases and pSP18 was cut with Pst and HindIII endonucleases. All resulting fragments were ligated together to form 7-14-89 #1-4. Acting as vector plasmid, 7-2-88 #1 was cut with HindIII and BglI endonucleases and plasmid 7-14-89 #1-4 was digested with HindII and BglI endonucleases, the resulting fragments isolated and re-ligated to form plasmid 8-17-89 #2-1.

Both nonduplicated (7-12-89 #3-4) and duplicated (8-17-89 #2-1) and terminatorless (7-2-88) constructs were excised as EcoR1/EcoR1 fragments and subcloned into the EcoR1 site of pAN70. Standard Agrobacterium triparental mating was employed using pRK2013 as the helper plasmid. DNA was confirmed by restriction and Southern blots.

Figure 6:
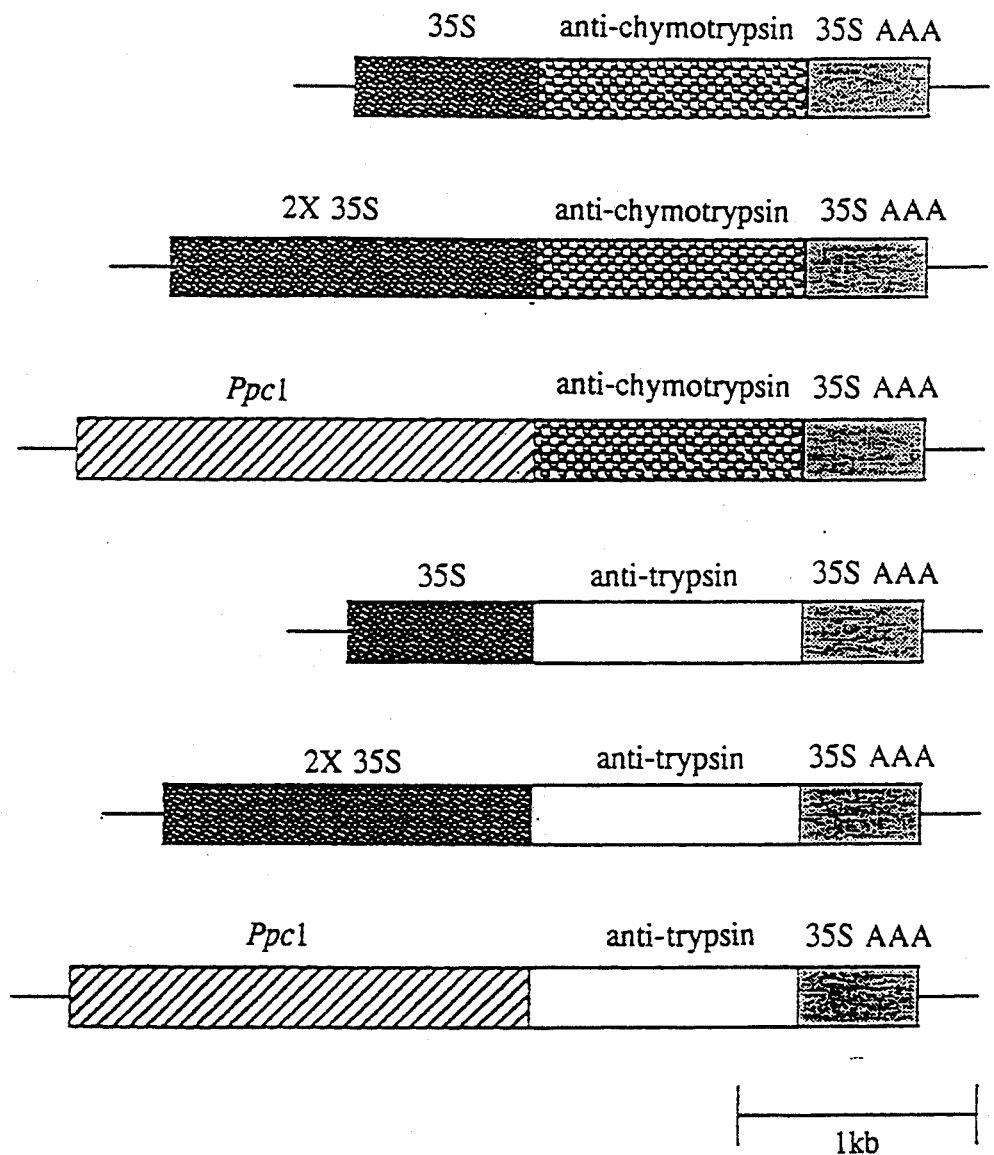
FIG. 6 is a diagram of proteinase inhibitor gene constructs designed for high-activity expression in plants. "Anti-chymotrypsin" and "anti-trypsin" refer to DNA encoding substrate specificity variants of *M. sexta* serpin. Promoters are designated as "35S" or "2X35S," referring to simple and tandem repeats of the CaMV 35S promoter, or "Ppc1" referring to phosphoenol pyruvate carboxylase promoter of *Mesembryanthemum crystallimium*. The polyadenylation signal region is designated "35S AAA."

Diagrams of the resulting constructs are shown in FIGS. 5 and 6.

Transformation System

Vegetative propagules were maintained axenically in culture vessels (GA-7, Magenta Corp., Chicago, Ill.) on Shenk and Hildebrandt medium (SH) with no growth regulators (SH-A). A 1.5 ml suspension of late log-phase alfalfa suspension culture cells was first spread on the surface of 50 ml of SH medium with 3% sucrose, 0.8% agar, 9 μM kinetin and 9 μM 2,4D (SH-B medium) in 100×20 mm petri dishes. Petiole and leaf segments from the above-mentioned axenic cultures were dissected into 2 mm pieces and dipped into a suspension (1×10$^9$ cells/ml) of *Agrobacterium tumefaciens* LBA4404 containing anti-elastase plasmid constructions inserted into pAN70 (FIG. 1). Leaf and petioles were co-cultivated for 72 hours on sterile filter paper resting on the spread suspension cells, which served as feeder cells. Following co-cultivation, explants were transferred to fresh SH-B with 500 μg/ml carbenicillin and 50 μg/ml of kanamycin. After 3 weeks, calli were subcultured on SH-B. Following 2 additional subcultures of arising callus on SH-B, at 4 week intervals, putative transformants were placed on SH-C medium, (SH-A with the addition of 300 μg/ml carbenicillin and 50 μg/ml kanamycin). Arising shoots were transferred to Magenta GA-7 jars containing SH-C medium. Later small 2-5 mm leaf segments were also removed and placed on SH-B medium with 50 μg/ml kanamycin. If callus grew easily from these explants then the NPT II gene was functional and the regenerated plants were considered transformed. Callus did not arise from control (non-transformed) leaf explants when placed on SH-B (with 50 μg/ml kanamycin). When plantlets had reached the five leaf stage and had good root development, they were transferred to Jiffy-7 peat pellets and grown in a high humidity chamber. Once roots were well established, the plants were potted in sterile soil and grown at 25° C. under a 16 h photoperiod. Transgenic plants were crossed as female parents with elite varieties that were highly fertile to obtain transgenic progeny.

Southern Analysis

DNA isolation, restriction, electrophoresis, blotting, random primer labeling, and hybridization conditions were as described (McCoy et al., 1991), except that 4 μg of DNA/lane was digested. Probe DNA was a 782 bp PCR fragment from *Manduca sexta* alaserpin cDNA used in the plant transformations. The PCR primers were GGCGAGACGGATCTGCAGAA (SEQ ID NO:16), complementary to nucleotide positions 73-92 of the cDNA sequence (Kanost et al., 1989) and CGCTCCTCAGCTCTTGAAAG (SEQ ID NO:17), complementary to nucleotide positions 835-854 of the cDNA. PCR conditions are as described (Echt et al., 1992).

Western Analysis

Total proteins were extracted in Smile E buffer (100 mM Tris HCl, pH 8.0; 100 mM NaCl; 20 mM EDTA; 10 mM DTT). Protein concentrations were estimated according to Ghosh et al., 1988. Following separation on 12.5% SDS-PAGE, the proteins were blotted to nitrocellulose (0.45 μM), and then reacted with a rabbit antibody directed against the PI (anti-elastase) of *Manduca sexta*. Development was using a 2° (goat anti-rabbit) antibody linked to peroxidase (Sigma).

In a series of tests aimed at the identification of an alfalfa variety easily transformed and regenerated, plant V-154 was found to be superior. Leaf and petiole sections from V-154 were efficiently transformed with the DNA constructs depicted in FIG. 5, and regenerated via somatic embryogenesis. Following transformation, the time for recovery of regenerated plantlets was not significantly different from nontransformed systems previously described (McCoy and Bingham, 1977). More than 200 transgenics containing the p35SPI-T construct from 30 independent explants were recovered. Over 250 transgenic plants containing either the Pcp1-PI-T construct (16 original explants) or the p2-35SPI and p2-35SPI-T 9 each represented by 27 explants) were obtained. Morphology was normal in the regenerated transgenic plants.

At least two plants from each of the original explants were tested and shown to contain the PI after southern analysis. After restriction, most plants showed a fragment which hybridized with the probe that migrated with the size expected for each construct. Some plants contained a single fragment greater than the expected size. Most of the transgenic plants regenerated from the same initial explant gave rise to similar southern hybridization patterns. For example, plants 1-1, 1-4 and 1-14 from explant #1 (p35SPI-T) all had the same 7 kb sized fragment. Some transgenic plants possessed additional bands that reacted with the probe. Plants from explant #36 contained the expected 2.8 kb band as well as a 4 kb fragment.

Immunological analysis confirmed that the single and the double 35S promoter (P-35SPI-T, p2-35SPI-T, and p2-35SPI) all functioned to promote the accumulation of the anti-elastase PI. All promoters were able to stimulate PI accumulation, however, the Pcp-1 promoter was not as effective as the 35S promoter derivatives (Table 3).

TABLE 3

| Construction | Plants Tested | PI Detected | % PI Detected |
| --- | --- | --- | --- |
| p2-35SPI | 8 | 4 | 50 |
| p2-35SPI-T | 15 | 10 | 67 |
| p35SPI-T | 23 | 14 | 61 |
| pPpcPI-T | 6 | 2 | 33 |
| NTF | 10 | 0 | 0 |

TABLE 3-continued

| Construction | Plants Tested | PI Detected | % PI Detected |
| --- | --- | --- | --- |
| (Control Plants[a]) | | | |

[a]Control plants are V-154 and unrelated elite plants used as males in crosses with transgenic plants.
The effect of promoter type on PI accumulation in primary regenerants from transgenic alfalfa. Data indicates the number of plants in which the PI (protein) was detected on a Western blot, using 30 μg of total protein per lane and an anti-PI antibody dilution 1:5000. Nontransformed (NTF) plants are included as controls.

There were at least three distinct species of protein that cross-reacted with the anti-elastase antibody. One PI species migrated as a 48 kD protein on SDS denaturing gels. Some transgenic plants accumulated a 44 kD species in addition to the 48 kD species. Both PI species accumulated in roots, leaves and flowers. However, the amount of accumulated PI of each protein size class differed with the tissue examined. Leaf tissue of plant 5-1 (construct p2-35SPI-T) showed greater accumulation of the 48 kD protein whereas root tissue accumulated the 44 kD species. Similar results were observed in root and leaf extracts of transgenic 73-2 (p2-35SPI). A large protein migrating with an apparent size of 120 kD also cross reacted with the anti-elastase antibody. The identity of this peptide is unclear, however, its appearance was only observed in transgenic plants that accumulated large quantities of the 48 kD PI species.

The presence or absence of the 19S terminator did not have a significant effect on the amount of PI accumulation (compare p2-35SPI and p2-35SPIT, Table 3). Transgenic plants with high levels of PI were detected with or without the 19S terminator.

To determine heritability of the PI, transgenic plants were crossed as females with untransformed and unrelated elite cultivars. Crosses were conducted in this manner because V-154 (whether normal or transformed) had poor male fertility. V-154 female fertility, although extremely low compared to elite alfalfa clones, was adequate to create and test the resultant progeny. To screen for genetic transmission in progeny plants, callus initiation and growth on kanamycin was employed. Leaf segments from the progeny plants were cultured on SH-B medium in the presence of 50 μg/ml kanamycin. Only plants that contained leaves that were positive for callus growth on SH-B were shown to accumulate the PI, anti-elastase.

We have observed that the onset of thrips predation in the greenhouse was delayed in the transgenic PI expressing plants as compared to the nontransformed plants (Table 4). Similar results have been observed on several occasions.

TABLE 4

| Individual Plant | Mean # Days Until Damage was Noticed |
| --- | --- |
| V-154 (Nontransformed) | 7 |
| 4-5 (P2-35SPI) | 24 |
| 11-3 (P2-35SPI) | 22 |
| 11-7 (P2-35SPI) | 25 |
| 12-1 (P2-35SPI) | 11 |
| 12-2 (P2-35SPI) | 14 |
| 56-2 (P2-35SPI) | 28 |
| 56-3 (P2-35SPI) | 26 |
| 73-2 (P2-35SPI) | 25 |

Damage after inoculation of transgenic alfalfa with thrips. Plants were either nontransformed (V-154) or transgenic individuals derived from p2-35SPI. Plants were placed in a greenhouse and exposed to thrips. Data represents the mean number of days (mean of three repetitions) that passed prior to observable thrips damage, as exemplified by emergence of malformed leaves.

EXAMPLE 8

Protection of cotton and tobacco against whitefly infestation.

The procedure used for the transformation and regeneration of Coker 312 is shown in Table 5. The use of 25 μg/ml of kanamycin as the selection for transformants proved effective. Initial studies with cotton used a 35S promoter fused to the reporter gene GUS, similar to that described by Jefferson (1987) Plant Mol. Biol. 5:387-405. Transformed cotton callus and embryos were found to contain significant GUS activity indicating the transformation and regeneration scheme was operational. Introduction of the various PI constructions depicted in FIGS. 1 and 2 followed the same below-mentioned procedure.

TABLE 5

Transformation and Regeneration of COKER 312 Cotyledon Explants

1. Surface sterilize seeds in 10% bleach for 10 minutes followed by extensive washes in sterile water. Seeds were placed on M&S medium (Murashige and Skoog, 1963) + 3% glucose and cultures were placed in a growth cabinet at 20° C. and 16 h light cycle, with approximately 250 μE m$^{-1}$sec$^{-1}$.
2. Three to fourteen days after sterilization, the cotyledons were excised and dipped into Agrobacterium at 1 × 10$^7$ cells/ml in M&S medium for 10 min. Explants were blotted dry and co-cultured for 3 days on M&S medium + 0.54 μM NAA (napthaleneacetic acid) and 24.6 μM 2iP (2-isopentyladenine).
3. Tissue was subcultured on identical medium + 400 μg/ml carbenicillin + 25 μg/ml kanamycin for 4 weeks. Growth conditions were as above.
4. In 3-4 weeks, resistant calli were transferred to the same medium as in step 3 and grown as before for four weeks.
5. Next calli were subcultured on hormoneless M&S medium for four weeks and grown for four weeks. Step 3 was repeated.
6. Growing calli were then transferred to M&S medium + 7.9 mM MgCl$_2$ + 19 mM KNO$_3$. After four weeks, calli were subcultured to similar medium. At this time embryos could often be seen within 4-12 weeks.
7. Embryo clusters were subcultured on to either M&S medium or M&S medium + 0.25 μM GA$_3$, 0.45 μM azetin, and 0.05 μM NAA. After at least 24 hours, tissue was transferred to hormoneless M&S medium + 0.5% charcoal, 7.9 mM MgCl$_2$ and 19 mM KNO$_3$. Embryos that do not germinate in 4-6 weeks were subcultured to identical medium.
8. Rooting plants were transferred to a hydroponic solution containing Hoagland's nutrient solution until root formation was extensive, then into soil in a high humidity chamber and hardened off.

Protein Analysis of Transgenic Plants

Protein extracts were made from tobacco and cotton transformed with the anti-elastase, anti-trypsin, and anti-chymotrypsin constructs. Anti-elastase was produced in only 40% of the transgenic tobacco plants. In transgenic cotton, all 35S (or 2X35S) promoter +PI genes were expressed, the levels of which depended on the tissue sampled. Similar results were observed for the anti-trypsin and anti-chymotrypsin inhibitors.

In regenerated transgenic tobacco and cotton the PIs were produced in planta and presented to the insect predator so that the toxin was ingested and would effect both lepidopteran (cotton boll worm) and coleopteran (boll weevil). The following data demonstrates a protective effect of the PIs to a serious cotton pest, *Bemisia tabaci* (white fly).

Transgenic tobacco plant having the anti-chymotrypsin inhibitor under the control of the double 35S promoter or under the control of the Ppc1 promoter were analyzed. The Ppc1 promoter produced little if any detectable PI, using Western analysis as the criteria. After attaining a height of 50-60 cm, plants were inoculated with at least 4 viable Poinsettia type white fly adults, from A and B biotype populations, using a clip cage. The A biotype population was reared on cotton while the B biotype was derived from infested zucchini plants. (See Costa, H. S. et al. (1992) J. Insect. Sci and Applic.) White flies were then removed after a few days after they had laid eggs. Thirty days later, the numbers of total and emerged egg cases were counted, as well as the numbers of developing and dead insect larvae.

Figure 7:
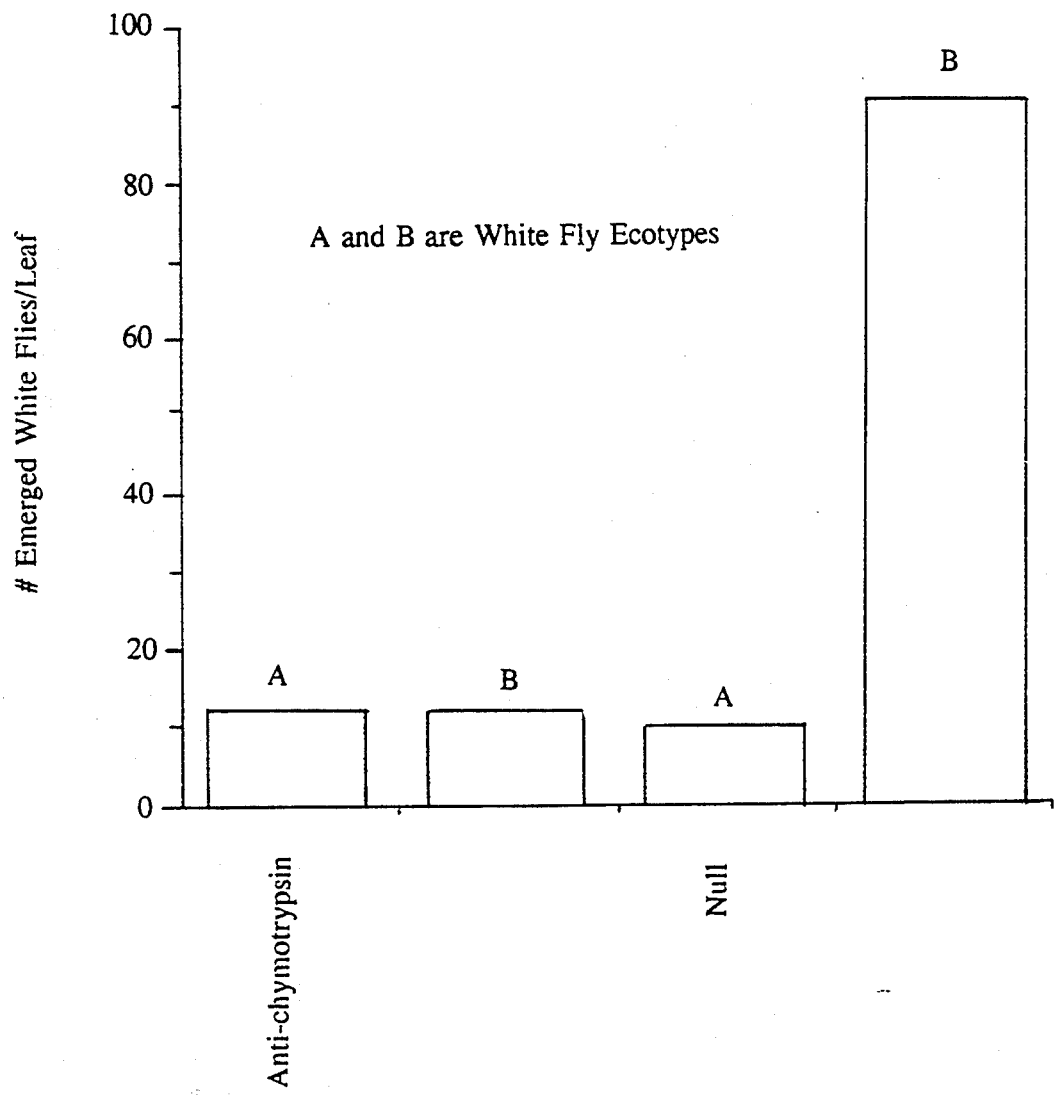
FIG. 7 is a bar graph of data on whitefly emergence on transgenic tobacco expressing an anti-chymotrypsin specificity variant of *M. sexta* serpin. As noted, "A" and "B" refer to separate whitefly biotypes.

The Ppc1 anti-chymotrypsin construction (no detectable PI protein): 12 larvae of A and B types emerged. Eggs were laid on an identical plant containing the 35S promoter driving the anti-chymotrypsin gene. In this plant the PI protein was accumulated in leaves. Results: no developing B type larvae were viable and few egg cases emerged. Six viable larvae of the A type were observed. This represents a decrease of 87% in the number of B type white flies which emerged from a transgenic tobacco expressing the anti-chymotrypsin gene (FIG. 7). A protective effect, as defined herein, was observed.

Anti-chymotrypsin PI provided a protective effect on tobacco against white fly infestation. Comparable results are observed in the transgenic cotton.

EXAMPLE 9

Tomato protection. Tomato plants transformed with Agrobacterium modified to transfer a *M. sexta* PI as described in Example 7 are protected from insect predation. In general, PI genes were cloned into plant expression cassettes and then subcloned between. the two T-DNA (transfer DNA) regions of a plasmid that confers kanamycin resistance in plants and can be grown in Agrobacterium too. Plant transformation is achieved by co-cultivating the Agrobacterium containing the plasmid with the PI gene of interest between the T-DNA regions on a medium that promotes plant single cell division. After 2-3 days, an explant is then transferred to medium containing the antibiotic carbenicillin, usually 300-400 ug/ml to kill the Agrobacterium. Additionally, the antibiotic kanamycin is added to 15-200 ug/ml. This is the selectable marker that will kill all nontransformed plant cells, while the transformed ones will grow. The tissue (callus) is then subcultured on a medium that allows shoot regeneration, the plantlet rooted, and then transferred to soil.

To sterilize tomato seeds the seeds are suspended in 15% bleach solution with 1 drop of Tween 20/250 ml. After 20 minutes, seeds are washed 3 times in sterile water and then soaked in sterile water for 10 minutes to 2 hours. Seeds are removed and placed in M&S #2 medium and to allow them to germinate at 25° C. with a 16 h light cycle.

After germination, when the first leaf appears, cotyledons are removed and cut into 0.2-0.5 cm² pieces in a liquid M&S #2 medium. One loop of Agrobacterium (grown on LB or M9) is suspended in M&S Medium #2. Explants are placed in the solution and allowed to incubate for 30 minutes. Explants are removed, blotted on sterile filter paper, and cocultured on JT-6 medium.

After 2-3 days, explants are transferred to fresh JT-6+400 ug/ml carbenicillin and 15-50 ug/ml kanamycin. This step kills the Agrobacterium and begins kanamycin selection. In three days, the explants are subcultured on new JT-6 medium. This step is essential.

After three weeks, small calli are cut away from the explant and subcultured on JT-7. Transfer to fresh JT-7 after 3-4 weeks. To root plantlets, shoots are cut off and placed in M&S #2 medium with only kanamycin. Plants are allowed to harden off and transferred to soil.

| TOMATO TISSUE CULTURE MEDIUM | | | |
|---|---|---|---|
|  | M&S Medium #2 | JT-6 | JT-7 |
| M&S Salts | 1 pkg | 1 pkg | 1 pkg |
| B-5 vitamins (100×) | 10 ml | 10 ml | 10 ml |
| Sucrose | 30 g | 30 g | 30 g |
| IAA (1 mg/ml) | — | 0.1 ml | — |
| Zeatin (1 mg/ml) | — | 0.5 ml | 1 ml |

Adjust volume to 1000 ml (1 liter), pH to 5.6–5.9 with 1 N KOH or HCl. Then add Bactoagar 7 g/liter, autoclave for 20 minutes. When cool add the antibiotics:
Carbenicillin (100 mg/ml)   3.0 ml 2.0 ml
Kanamycin (50 mg/ml)   3.0 ml 2.0 ml Swirl medium and pour in a sterile hood. Allow medium to gal at least for several hours, to preferably overnight.

To prepare zeatin, dissolve 0.01 g (10 mg) in 1 ml 1N HCl, and add 9 ml of water when dissolved. This is a 1 mg/ml stock. Zeatin can easily withstand heating.

IAA is sensitive to light and does break down in stock solutions. Normally, IAA is prepared just before use by dissolving 0.01g (10 mg) in 1 ml of 1N KOH, then when dissolved, 9 ml of water is added. this is a 1 mg/ml stock. Add IAA before autoclaving. Some IAA will be degraded in the autoclave, however, the amount undestroyed will be sufficient to encourage calli formation. Note: if one intends to filter sterilize IAA the concentration must be reduced approximately 3 times.

The *M. sexta* PI and its variants having anti-trypsin or anti-chymotrypsin activity provide a protective effect against insect predation in transgenic plants expressing the PI. The findings disclosed herein for transgenic alfalfa, cotton and tobacco can be extended to other transformable and regenerable plats, using techniques available to those of ordinary skill in the art. The choice of promoters to affect expression levels desired is also one which those skilled in the art can make from a wide variety of available promotes, without undue experimentation. Similarly, protection can be optimized by selecting the optimal PI substrate specificity for each susceptible insect. Since the transgenic PI-expressing plants are readily grown in quantity, screening for insect susceptibility can be accomplished as a routine exercise. Furthermore, it will be understood that where a protective effect against a first insect pest has been demonstrated for a given plant species, protection against a second susceptible insect pest of the same plant species will occur as a matter of course. Protection against the second insect pest can be optimized by providing for expression at optimized time, amount and plant tissue type, as is well-known in the art. Further modifications, optimizations, extensions and extrapolations following the teachings of the present disclosure as may occur to those of ordinary skill in the art are described as part of the present invention.

---

We claim:

1. A transgenic plant selected from the group consisting of cotton, alfalfa and tobacco, comprising a gene encoding an expressible serine proteinase inhibitor of *Manduca sexta*.

2. A plant according to claim 1 comprising cotton.

3. A plant according to claim 1 comprising alfalfa.

4. A plant according to claim 1 comprising tobacco.

5. A purified DNA segment comprising a coding sequence having a 5'-end and a 3'-end encoding a serine proteinase inhibitor of *Manduca sexta* and a promoter at the 5'-end of the coding sequence, the promoter being capable of providing expression of the coding sequence in a plant cell.

6. The DNA segment of claim 5 wherein the coding sequence encodes unmodified *M. sexta* alaserpin.

7. The DNA segment of claim 5 wherein the coding sequence encodes a variant *M. sexta* proteinase inhibitor having chymotrypsin inhibitory activity.

8. The DNA segment of claim 5 wherein the coding sequence encodes a variant *M. sexta* proteinase inhibitor having trypsin inhibitory activity.

9. The DNA segment of claim 5 wherein the promoter is a promoter of a plant gene.

10. The DNA segment of claim 5 wherein the promoter is a promoter of a plant virus.

11. The DNA segment of claim 5 wherein the promoter is a promoter of the T-DNA of an Agrobacterium species.

12. A method for providing a protective effect against insect damage to a plant selected from the group consisting of cotton, alfalfa and tobacco comprising the step of expressing within a plant cell a transgene encoding a serine proteinase inhibitor of *Manduca sexta* whereby an insect feeding on a plant comprising said plant cell contacts the proteinase inhibitor, said protective effect being of sufficient magnitude to be statistically significant when compared to a control where no transgene encoding a serine proteinase inhibitor is present.

13. A method for providing a protective effect against insect damage to a plant selected from the group consisting of cotton, alfalfa and tobacco comprising the step of providing a serine proteinase inhibitor of *Manduca sexta* on the surface of a plant or within tissues of a plant, whereby an insect feeding on said plant contacts the proteinase inhibitor, said protective effect being of sufficient magnitude to be statistically significant when compared to a control where no proteinase inhibitor is present.

14. A plant according to claim 1 wherein the inhibitor of *Manduca sexta* has anti-trypsin activity.

15. A plant according to claim 1 wherein the inhibitor of *Manduca sexta* has anti-chymotrypsin activity.

16. A plant according to claim 1 wherein the inhibitor of *Manduca sexta* has anti-elastase activity.

* * * * *